(12) United States Patent
Shang et al.

(10) Patent No.: US 7,226,649 B2
(45) Date of Patent: Jun. 5, 2007

(54) LASER WELDABLE FLEXIBLE MEDICAL TUBINGS, FILMS AND ASSEMBLIES THEREOF

(75) Inventors: Sherwin Shang, Vernon Hills, IL (US); Tahua Yang, Woodridge, IL (US); Zenichiro Kai, Gurnee, IL (US); Frank Lanherr, Cary, IL (US); Martin F. Miller, Lake in the Hills, IL (US); Larry A. Rosenbaum, Gurnee, IL (US)

(73) Assignee: Baxter International Inc., Deerfield, IL (US)

(*) Notice: Subject to any disclaimer, the term of this patent is extended or adjusted under 35 U.S.C. 154(b) by 219 days.

(21) Appl. No.: 10/251,682

(22) Filed: Sep. 20, 2002

(65) Prior Publication Data

US 2003/0141634 A1     Jul. 31, 2003

Related U.S. Application Data

(63) Continuation-in-part of application No. 10/061,835, filed on Jan. 31, 2002, now Pat. No. 6,913,056.

(51) Int. Cl.
| | |
|---|---|
| B32B 1/08 | (2006.01) |
| B32B 27/08 | (2006.01) |
| B32B 37/06 | (2006.01) |
| F16L 11/06 | (2006.01) |
| F16L 11/20 | (2006.01) |
| A61M 1/00 | (2006.01) |
| A61M 1/28 | (2006.01) |
| B29C 65/16 | (2006.01) |
| B29D 22/00 | (2006.01) |
| B29D 23/00 | (2006.01) |

(52) U.S. Cl. .............. 428/35.7; 428/36.9; 428/36.91; 428/36.92; 138/137; 138/140; 138/DIG. 7; 604/29; 156/272.8

(58) Field of Classification Search ............ 428/35.7, 428/36.9, 36.91, 36.92; 138/137, 140, DIG. 7; 604/29; 156/272.8
See application file for complete search history.

(56) References Cited

U.S. PATENT DOCUMENTS 3,063,890 A    11/1962    Saumsiegle .............. 156/308.4

(Continued)

FOREIGN PATENT DOCUMENTS

BR        9705844      6/1999

(Continued)

OTHER PUBLICATIONS web page http:--www.cellrobtics.com-perslasette.html printed on Aug. 3, 2001.

(Continued)

*Primary Examiner*—Alicia Chevalier
*Assistant Examiner*—Chris Bruenjes
(74) *Attorney, Agent, or Firm*—Ira D. Finkelstein; Paula J. F. Kelly

(57) ABSTRACT

The present invention provides a tubing assembly having a sidewall having a first layer. The first layer is fabricated from a first polymer blend comprising a first component of a material not thermally responsive to laser beam and selected from the group consisting of polyolefins, ethylene and lower alkyl acrylate copolymers, ethylene and lower alkyl substituted alkyl acrylate copolymers, ethylene vinyl acetate copolymers, polybutadienes, polyesters, polyamides, and styrene and hydrocarbon copolymers. A second component of the blend is a laser responsive material having low solubility in aqueous medium; and the blend being sufficiently thermally responsive to exposure to a laser beam having a wavelength within a range of wavelengths from about 700 nm to about 1500 nm to melt upon exposure to the laser beam for a short period of time. The assembly also has an end cap film covering the fluid outlet.

32 Claims, 16 Drawing Sheets

U.S. PATENT DOCUMENTS

| | | | |
|---|---|---|---|
| 3,542,712 A | 11/1970 | Gorton et al. | 524/277 |
| 3,645,939 A | 2/1972 | Gaylord et al. | 525/54.23 |
| 3,725,174 A | 4/1973 | Gaylord et al. | 156/305 |
| 3,734,819 A | 5/1973 | Knutson | 428/463 |
| 3,763,073 A | 10/1973 | Knutson | 524/776 |
| 3,767,633 A | 10/1973 | Dietrich | 526/81 |
| 3,956,230 A | 5/1976 | Gaylord | 523/209 |
| 4,029,850 A | 6/1977 | Ishii et al. | 428/518 |
| 4,037,020 A | 7/1977 | Ishii et al. | 428/518 |
| 4,046,728 A | 9/1977 | Harmuth | 523/437 |
| 4,071,494 A | 1/1978 | Gaylord | 523/205 |
| 4,089,726 A | 5/1978 | Ishii et al. | 156/244.23 |
| 4,126,504 A | 11/1978 | Wolinski et al. | 156/310 |
| 4,210,567 A | 7/1980 | Kosters | 524/290 |
| 4,230,774 A | 10/1980 | Watts et al. | 428/518 |
| 4,316,832 A | 2/1982 | Walkden | 524/775 |
| 4,322,516 A | 3/1982 | Wiest et al. | 523/307.7 |
| 4,327,726 A | 5/1982 | Kwong et al. | 604/262 |
| 4,369,779 A | 1/1983 | Spencer | 604/29 |
| 4,410,026 A | 10/1983 | Boggs et al. | 383/60 |
| 4,412,835 A | 11/1983 | Spencer | 604/29 |
| 4,417,753 A | 11/1983 | Bacehowski et al. | 285/21.1 |
| 4,439,192 A | 3/1984 | Leurink | 604/408 |
| 4,488,961 A | 12/1984 | Spencer | 210/136 |
| 4,495,312 A | 1/1985 | Hata et al. | 523/105 |
| 4,496,362 A | 1/1985 | Leurink | 604/408 |
| 4,507,119 A | 3/1985 | Spencer | 156/152 |
| 4,511,354 A * | 4/1985 | Sterling | 604/98.01 |
| 4,516,971 A | 5/1985 | Spencer | 156/159 |
| 4,516,977 A | 5/1985 | Herbert | 604/415 |
| 4,525,234 A | 6/1985 | Herold et al. | 156/332 |
| 4,587,289 A | 5/1986 | Comert et al. | 524/505 |
| 4,601,948 A | 7/1986 | Lancaster et al. | 428/349 |
| 4,610,670 A | 9/1986 | Spencer | 604/29 |
| 4,614,208 A * | 9/1986 | Skarelius | 138/103 |
| 4,619,642 A | 10/1986 | Spencer | 604/29 |
| 4,650,220 A | 3/1987 | Grabowski | 285/21.1 |
| 4,663,032 A | 5/1987 | Loos et al. | 210/97 |
| 4,664,658 A | 5/1987 | Sawada et al. | 604/266 |
| 4,687,474 A | 8/1987 | Takanashi | 604/257 |
| 4,707,389 A | 11/1987 | Ward | 428/36.6 |
| 4,720,524 A | 1/1988 | Ohmae et al. | 525/173 |
| 4,723,947 A | 2/1988 | Konopka | 604/272 |
| 4,725,641 A | 2/1988 | Comert et al. | 524/499 |
| 4,726,960 A | 2/1988 | Sawada et al. | 427/2.28 |
| 4,737,214 A | 4/1988 | Leurink et al. | 156/158 |
| 4,739,012 A | 4/1988 | Hagman | 525/92 A |
| 4,740,017 A | 4/1988 | Grabowski | 285/21.1 |
| 4,753,697 A | 6/1988 | Spencer et al. | 156/158 |
| 4,770,735 A | 9/1988 | Spencer et al. | 156/258 |
| 4,771,106 A | 9/1988 | Ohmae et al. | 525/65 |
| 4,784,409 A | 11/1988 | Piechowiak | 285/21.1 |
| 4,793,880 A | 12/1988 | Spencer et al. | 156/158 |
| 4,827,099 A | 5/1989 | Krebs et al. | 219/121.63 |
| 4,832,773 A | 5/1989 | Spencer et al. | 156/158 |
| 4,848,801 A | 7/1989 | Grabowski | 285/21.1 |
| 4,864,101 A | 9/1989 | Shaposka et al. | 219/243 |
| 4,865,902 A | 9/1989 | Golike et al. | 428/215 |
| 4,880,873 A | 11/1989 | Sagane | 525/61 |
| 4,897,138 A | 1/1990 | Shaposka et al. | 156/158 |
| 4,900,771 A | 2/1990 | Gerace et al. | 524/296 |
| 4,913,756 A | 4/1990 | Shaposka et al. | 156/158 |
| 4,927,184 A | 5/1990 | Bourjot et al. | 285/21.1 |
| 4,933,036 A | 6/1990 | Shaposka et al. | 156/158 |
| 4,948,643 A | 8/1990 | Mueller | 428/36.6 |
| 4,997,430 A | 3/1991 | Van der Heiden et al. | 604/414 |
| 5,026,019 A | 6/1991 | Biekart et al. | 251/4 |
| 5,037,395 A | 8/1991 | Spencer | 604/113 |
| 5,039,768 A | 8/1991 | Gerace et al. | 526/279 |
| 5,061,451 A | 10/1991 | Ganshirt et al. | 422/101 |
| 5,088,994 A | 2/1992 | Porat et al. | 604/408 |
| 5,135,600 A | 8/1992 | Ishida | 156/308.6 |
| 5,141,592 A | 8/1992 | Shaposka et al. | 156/515 |
| 5,156,701 A | 10/1992 | Spencer et al. | 156/158 |
| 5,158,630 A | 10/1992 | Shaposka et al. | 156/158 |
| 5,166,269 A | 11/1992 | Wietsma et al. | 525/214 |
| 5,179,496 A | 1/1993 | Mimura | 361/154 |
| 5,188,697 A | 2/1993 | Lueghamer et al. | 156/499 |
| 5,209,800 A | 5/1993 | Spencer et al. | 156/158 |
| 5,224,937 A | 7/1993 | van der Heiden | 604/200 |
| 5,244,522 A | 9/1993 | Spencer et al. | 156/158 |
| 5,248,359 A | 9/1993 | Shaposka et al. | 156/158 |
| 5,248,562 A | 9/1993 | Palermo et al. | 428/522 |
| 5,250,607 A | 10/1993 | Comert et al. | 524/507 |
| 5,254,825 A | 10/1993 | Schippers | 219/769 |
| 5,256,229 A | 10/1993 | Spencer | 156/158 |
| 5,256,845 A | 10/1993 | Schippers | 219/769 |
| 5,272,304 A | 12/1993 | Been et al. | 219/769 |
| 5,274,035 A | 12/1993 | Chundury | 525/92 A |
| 5,279,685 A | 1/1994 | Ivansons et al. | 156/158 |
| 5,324,233 A | 6/1994 | Owensby et al. | 493/190 |
| 5,336,351 A | 8/1994 | Meyers | 156/158 |
| 5,342,345 A | 8/1994 | Spencer | 604/408 |
| 5,356,709 A | 10/1994 | Woo et al. | 428/376 |
| 5,367,010 A | 11/1994 | Gervase et al. | 524/260 |
| 5,368,586 A | 11/1994 | Van Der Heiden et al. | 604/403 |
| 5,371,767 A | 12/1994 | Pirl | 376/260 |
| 5,385,979 A | 1/1995 | Osawa et al. | 525/145 |
| D355,848 S | 2/1995 | Ivansons et al. | D9/415 |
| 5,391,610 A | 2/1995 | Comert et al. | 524/507 |
| 5,397,425 A | 3/1995 | Ivansons et al. | 156/503 |
| 5,407,742 A | 4/1995 | Tavss et al. | 428/34.2 |
| 5,410,131 A | 4/1995 | Brunet et al. | 219/535 |
| D357,926 S | 5/1995 | Ivansons et al. | D15/139 |
| 5,439,454 A | 8/1995 | Lo et al. | 604/264 |
| 5,460,625 A | 10/1995 | Johnson | 604/403 |
| 5,464,496 A | 11/1995 | Wilson et al. | 156/499 |
| 5,476,718 A | 12/1995 | Ichizuka et al. | 428/424.6 |
| 5,484,375 A | 1/1996 | Owensby et al. | 493/190 |
| 5,486,210 A | 1/1996 | Kerr et al. | 8/115.66 |
| 5,492,963 A | 2/1996 | Ozawa et al. | 524/576 |
| 5,496,291 A | 3/1996 | Spencer | 604/523 |
| 5,518,575 A | 5/1996 | Watanabe | 156/494 |
| 5,520,218 A | 5/1996 | Hlavinka et al. | 138/89 |
| 5,525,186 A | 6/1996 | Ivansons et al. | 156/503 |
| 5,534,591 A | 7/1996 | Ozawa et al. | 525/194 |
| 5,554,253 A | 9/1996 | Watanabe | 156/503 |
| 5,601,889 A | 2/1997 | Chundury et al. | 428/34.3 |
| 5,620,738 A | 4/1997 | Fan et al. | 427/2.3 |
| 5,632,852 A | 5/1997 | Ivansons et al. | 156/503 |
| 5,656,345 A | 8/1997 | Strand et al. | 428/36.9 |
| 5,674,333 A | 10/1997 | Spencer | 156/64 |
| 5,686,527 A | 11/1997 | Laurin et al. | 525/66 |
| 5,733,268 A | 3/1998 | Spencer | 604/523 |
| 5,749,414 A | 5/1998 | Damsohn et al. | 165/178 |
| 5,802,689 A | 9/1998 | Sano | 29/33 T |
| 5,810,792 A | 9/1998 | Fangrow et al. | 604/533 |
| 5,821,293 A | 10/1998 | Roesch et al. | 524/365 |
| 5,824,724 A | 10/1998 | Roesch et al. | 524/365 |
| 5,849,843 A | 12/1998 | Laurin et al. | 525/66 |
| 5,854,347 A | 12/1998 | Laurin et al. | 525/66 |
| 5,855,731 A | 1/1999 | Spencer | 156/503 |
| 5,871,612 A | 2/1999 | Spencer | 156/503 |
| 5,877,236 A | 3/1999 | Roesch et al. | 523/210 |
| 5,879,318 A | 3/1999 | Van Der Heiden et al. | 604/6.02 |
| 5,891,539 A * | 4/1999 | Nakane et al. | 428/36.9 |
| 5,919,173 A | 7/1999 | Spencer | 604/523 |
| 5,921,587 A | 7/1999 | Lueghamer | 285/21.2 |
| 5,922,798 A | 7/1999 | Roesch et al. | 524/360 |
| 5,928,216 A | 7/1999 | Spencer | 604/523 |
| 5,935,847 A | 8/1999 | Smith et al. | 435/297.5 |
| 5,964,261 A | 10/1999 | Neuenfeldt et al. | 141/327 |
| 5,968,380 A | 10/1999 | Hayashi | 219/121.64 |

| | | | | | | |
|---|---|---|---|---|---|---|
| 5,993,949 A | 11/1999 | Rosenbaum et al. ......... 428/213 | JP | 1210486 | 8/1989 | |
| 5,998,019 A | 12/1999 | Rosenbaum et al. ......... 428/345 | JP | 2113052 | 4/1990 | |
| 6,004,311 A | 12/1999 | Heilmann et al. ........... 604/533 | JP | 02269753 A2 | 11/1990 | |
| 6,004,417 A | 12/1999 | Roesch et al. ............... 156/155 | JP | 3120042 | 5/1991 | |
| 6,022,344 A | 2/2000 | Meijer ......................... 604/533 | JP | 3177682 | 8/1991 | |
| 6,024,220 A | 2/2000 | Smith et al. ................. 206/484 | JP | 4208419 | 7/1992 | |
| 6,026,882 A | 2/2000 | Yamada et al. ............. 156/433 | JP | 5042640 | 2/1993 | |
| 6,071,690 A | 6/2000 | Spencer .......................... 435/2 | JP | 5124146 | 5/1993 | |
| 6,083,584 A | 7/2000 | Smith et al. ............... 428/35.2 | JP | 6-91010 | 4/1994 | |
| 6,094,969 A | 8/2000 | Loos et al. ...................... 73/37 | JP | 6-91011 | 4/1994 | |
| 6,132,833 A | 10/2000 | Spencer ...................... 428/64.1 | JP | 6-233817 | 8/1994 | |
| 6,149,997 A | 11/2000 | Patel et al. ............... 428/36.91 | JP | 08003526 A2 | 1/1996 | |
| 6,168,862 B1 | 1/2001 | Rosenbaum et al. ......... 428/345 | JP | 08003527 A2 | 1/1996 | |
| 6,225,404 B1 | 5/2001 | Sorensen et al. ........... 525/54.1 | JP | 08295862 A2 | 11/1996 | |
| 6,251,202 B1 | 6/2001 | Murphy ......................... 156/64 | JP | P2000-126288 A | 5/2000 | |
| 6,261,655 B1 | 7/2001 | Rosenbaum et al. ....... 428/36.7 | JP | 2000170967 | 6/2000 | |
| 6,270,599 B1 | 8/2001 | Wood ........................... 156/64 | JP | 2000301592 | 10/2000 | |
| 6,293,594 B1 | 9/2001 | Safarevich et al. ......... 285/21.1 | JP | 2000344852 A2 | 12/2000 | |
| 6,296,730 B1 | 10/2001 | Williams et al. .............. 156/94 | JP | 2002146303 A2 | 5/2002 | |
| 6,297,046 B1 | 10/2001 | Smith et al. ............. 435/297.5 | NL | 8 101 391 | 10/1982 | |
| 6,299,596 B1 | 10/2001 | Ding ........................ 604/96.01 | WO | WO 8300699 | 3/1983 | |
| 6,302,151 B1 | 10/2001 | Maitay ........................ 138/125 | WO | WO 9315908 A1 | 8/1993 | |
| 6,308,882 B1 | 10/2001 | Shuster et al. ............... 228/175 | WO | WO 9604704 | 2/1996 | |
| 6,333,122 B1 | 12/2001 | Furukawa et al. ........... 428/690 | WO | WO 9836902 A1 | 8/1998 | |
| 6,368,315 B1 | 4/2002 | Gillis et al. .................. 604/523 | WO | WO 9924242 A1 | 5/1999 | |
| 6,399,704 B1 | 6/2002 | Laurin et al. .................. 525/66 | WO | WO 0005316 | 2/2000 | |
| 6,465,068 B1 | 10/2002 | Patel et al. ............... 428/36.91 | WO | WO 0146332 A1 | 6/2001 | |
| 2003/0039837 A1* | 2/2003 | Koshida et al. ........... 428/411.1 | WO | WO 0160586 A1 | 8/2001 | |
| 2003/0124285 A1* | 7/2003 | Hopcus et al. .............. 428/36.9 | WO | WO 0162314 A2 | 8/2001 | |
| | | | WO | WO 0166662 | 9/2001 | |
| | | | WO | WO 0185417 | 11/2001 | |

FOREIGN PATENT DOCUMENTS

| | | |
|---|---|---|
| CA | 1205783 | 6/1986 |
| CN | 1052131 | 6/1991 |
| DE | 3 734 170 | 4/1989 |
| EP | 307546 | 3/1989 |
| EP | 0 406 485 A | 1/1991 |
| EP | 418772 | 3/1991 |
| EP | 0 583 582 A1 | 2/1994 |
| EP | 0 619 175 A2 | 10/1994 |
| EP | 0 508 251 B1 | 8/1995 |
| EP | 0 689 846 A1 | 1/1996 |
| EP | 0 723 851 A2 | 7/1996 |
| EP | 0 725 134 A2 | 8/1996 |
| EP | 564231 B1 | 5/1997 |
| EP | 0 515 811 B1 | 8/2000 |
| EP | 1 064 960 A2 | 1/2001 |
| FR | 1471450 | 3/1967 |
| JP | 46042639 | 12/1971 |
| JP | 72044977 | 11/1972 |
| JP | 48089236 | 11/1973 |
| JP | 75016826 | 6/1975 |
| JP | 53014772 A | 2/1978 |
| JP | 57150533 | 9/1982 |
| JP | 58124648 | 7/1983 |
| JP | 58132552 | 8/1983 |
| JP | 62244614 | 10/1987 |
| JP | 63126709 | 5/1988 |

OTHER PUBLICATIONS web page http:--www.laserweld.com-laser-welding.html printed on Mar. 21, 2001.
web page http:--www.coherentic.com-html-about.html printed on Mar. 21, 2001.
web page www.dencotcd.com.
LaseRevolution, Inc. web page printed Mar. 21, 2001.
Joining Technologies LLC web page, "Electron Beam Welding", printed Mar. 20, 2001.
Ebeam web page printed Mar. 20, 2001.
Dimetrics,Inc. web page printed Mar. 20, 2001.
MPW web page printed Mar. 20, 2001.
Fresenius HemoCare, Inc. web page printed Jun. 6, 2002.
Joining Technologies web page, "Weld Joint Design", printed Mar. 21, 2001.
Electrox—Manufacturing Solutions web page printed Mar. 21, 2001.
TWI Technology web page printed Mar. 21, 2001.
Joining Technologies, "Laser Beam Welding", printed Mar. 21, 2001.
Search Report dated Jul. 5, 2002.
Industrial Microphotonics Company web page printed Mar. 21, 2001.

* cited by examiner

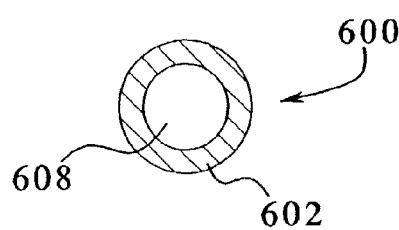 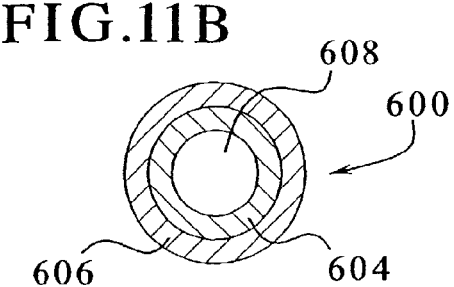
FIG.11A  FIG.11B
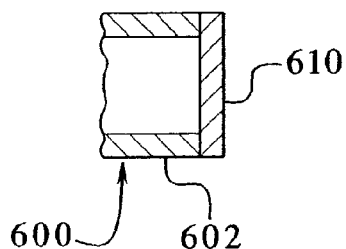 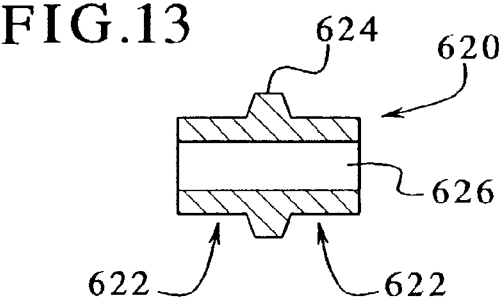
FIG.12  FIG.13
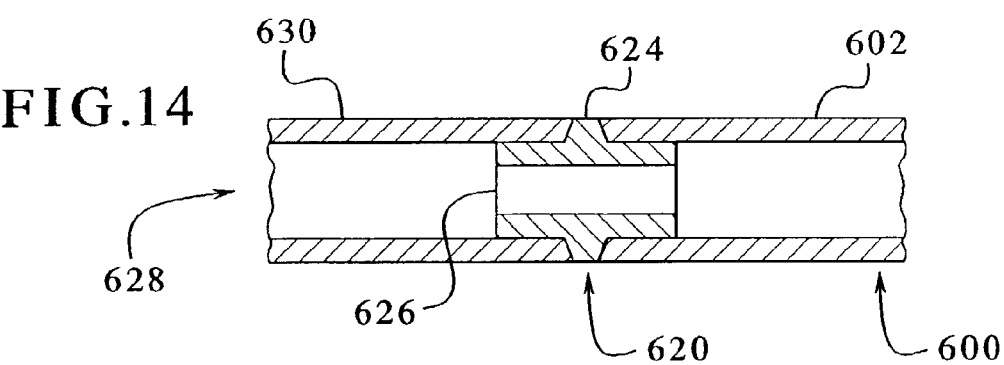
FIG.14
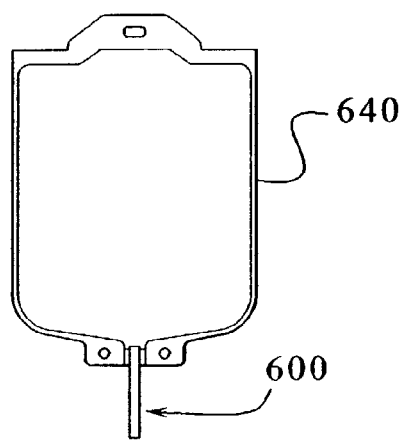 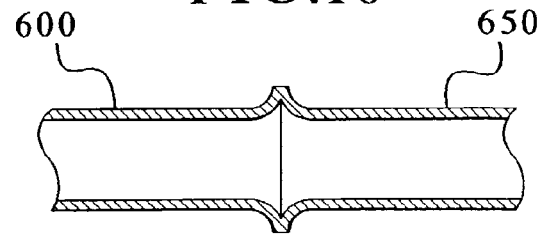
FIG.15  FIG.16

LASER WELDABLE FLEXIBLE MEDICAL TUBINGS, FILMS AND ASSEMBLIES THEREOF

RELATED APPLICATIONS

This is a continuation in part of U.S. patent application Ser. No. 10/061,835 filed on Jan. 31, 2002, now U.S. Pat. No. 6,913,056, and which is hereby incorporated herein by reference and made a part hereof.

FEDERALLY SPONSORED RESEARCH OR DEVELOPMENT

Not Applicable.

BACKGROUND OF THE INVENTION

The present invention relates to laser-weldable flexible tubing that is particularly well suited for use in the delivery of therapeutic solutions such as peritoneal dialysis solutions.

It is known to use medical containers with tubing for various medical procedures such as kidney dialysis, intravenous delivery of therapeutic fluids, delivery of nutritional fluids; delivery of blood, blood components, and blood substitutes. Fluid containers and tubing are also widely used in other industries such as the food industry and the chemical industries.

For example, flexible medical tubings are used in systems for treating renal disease. In renal failure of any cause, there are several physiological derangements. The balance of water, minerals and the excretion of daily metabolic load is no longer possible in renal failure. During renal failure, toxic end products of nitrogen metabolism (urea, creatinine, uric acid and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys. Hemodialysis and peritoneal dialysis are two types of dialysis therapies commonly used to treat loss of kidney function.

In general, hemodialysis treatment removes waste, toxins, and excess water from the patient's blood. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, waste, toxins, and excess water are removed from the patient's blood and the blood is infused back into the patient. Many tubes are used in the process that must be connected or disconnected. Hemodialysis treatment lasts several hours and is generally performed in a treatment center about three or four times per week.

Peritoneal dialysis, typically, utilizes a dialysis solution, or dialysate, which is infused into a patient's peritoneal cavity. The dialysate contacts the patient's peritoneal membrane in the peritoneal cavity. Waste, toxins and excess water pass from the patient's bloodstream through the peritoneal membrane and into the dialysate. The transfer of waste, toxins and water from the bloodstream into the dialysate occurs due to diffusion and osmosis, i.e., there is an osmotic gradient across the membrane. The spent dialysate is drained from the patient's peritoneal cavity to remove the waste, toxins and water from the patient. After the spent dialysis is drained, it is replaced with a fresh dialysate solution.

While the present invention has application in connecting or disconnecting tubes for medical procedures, the following discussion focuses, as an example, on a particular tube connection and disconnection processes performed during peritoneal dialysis. Numerous tubes are used in the process that must be connected or disconnected. In peritoneal dialysis, patients have a catheter implanted in their peritoneal cavity with an end protruding from the patient. The protruding end of the catheter terminates with a section of tubing known as a transfer set. The transfer set is typically made from a silicone material and must be periodically replaced say every several months. The transfer set is provided to connect the patient to dialysate fluid bags or discharge bags. The transfer set typically has a spike that connects to an access port positioned in a tube associated with the drain bag or dialysate solution bag (dialysate set). In general, the patient manually stabs the port with the spike to connect the transfer set to the dialysate set. The patient connects the tube in the transfer set to a drain to allow spent dialysate fluid to drain from the peritoneal cavity. Next, the patient is connected to a bag of fresh dialysate and manually infuses the fresh dialysate through the catheter and into the patient's peritoneal cavity. When the patient completes treatment, the port is pulled off the spike and a cap is placed on the spike until the patient is ready for the next treatment. When the patient disconnects the catheter from the fresh dialysate bag, the dialysate dwells within the peritoneal cavity to draw waste, toxins and excess water from the patient's bloodstream to the dialysate solution. After the dwell period, the patient repeats the manual dialysis procedure and drains the spent dialysate from the peritoneal cavity.

Accordingly, during dialysis treatments such as those described above, the patient is required to connect and disconnect the catheter and transfer set from the fill or drain line (or tube) a number of times. Some devices are available today to assist the patient during the process when using specialized sterilization equipment. However, by and large, these connections and disconnections are performed manually.

One such device, incorporates a heated wafer or hot knife that physically contacts the tubing to cut it by melting the tube and joining two tubes together or melt-sealing the tube ends. Typically, heated wafer applications involve a "melt and wipe" process. In peritoneal dialysis, for example, a patient must drain spent dialysate or replenish his/her peritoneal cavity with fresh dialysate. To this end, the patient must connect the transfer set tubing to a tube extending from either a drain bag or a bag containing fresh dialysate. In one "melt and wipe" process, the transfer set tubing is bent in a U or V-shape to fit into a U or V-shaped tube holder. Similarly, the bag-side tube is bent in a U or V-shape to fit into another U or V-shaped tube holder adjacent the first tube holder. A heated wafer moves across the space between the two tube holders and physically contacts the tubing at the bend junction of the U-shape or V-shape. As the heated wafer contacts the tubing, it melts the tube at the bend junction of the U-shape or V-shape. The wafer then wipes the melted tubing material and removes the material from the area between the tube holders. The two holders are brought together and two connections are made. In the first connection, the transfer set tubing is connected to the bag-side tube and the dialysis process is ready to begin. In the second connection, the wasted tube material from the transfer set tubing and the bag-side tube is connected together and discarded.

In order to disconnect the patient from the bag, hot knives are used to cut the tube. An example of a known disconnecting process with the hot knife involves two tubes that are placed side by side across two tube holders. One of the tubes is a short tube having two sealed ends. Generally, the tube holders include a ridge at one end of the tube holder to flatten a portion of the tube to stop fluid flow. The hot knife severs each tube into two pieces. After the hot knife cuts the tube, one of the tube holders moves in relation to the other tube holder. The tubing is "swapped," realigned with one of the cut portions of the short tube, and connected to it—thus, a disconnection is made between the patient and the bag.

These devices have a relatively low level of reliability due to the inconsistency in melting and cutting processes. This inconsistency can result in imperfect seals, leading to leaks, bacterial infiltration and, ultimately, the patient may well experience, among other things, infection or peritonitis. Also, none of these known methods inspect the integrity of the weld formed between the two tube ends during the connection process. Thus, users must rely on their own visual inspection of the weld.

Moreover, these devices are not user friendly. Often times, patients that need dialysis treatment are visually or otherwise impaired. For example, some dialysis patients experience manual dexterity problems. Many of the known processes involve a great deal of human interaction with loading the tubes into the tube holders. Also, the equipment should be cleaned and the heated wafer replaced after each use to avoid contamination. Thus, this is a difficult process for visually impaired patients and those with poor manual dexterity.

SUMMARY OF THE INVENTION

The present invention provides a tubing assembly having a sidewall having a first layer. The first layer is fabricated from a first polymer blend comprising a first component of a material not thermally responsive to laser beam and selected from the group consisting of polyolefins, ethylene and lower alkyl acrylate copolymers, ethylene and lower alkyl substituted alkyl acrylate copolymers, ethylene vinyl acetate copolymers, polybutadienes, polyesters, polyamides, and styrene and hydrocarbon copolymers. A second component of the blend is a laser responsive material having low solubility in aqueous medium; and the blend being sufficiently thermally responsive to exposure to a laser beam having a wavelength within a range of wavelengths from about 700 nm to about 1500 nm to melt upon exposure to the laser beam for a short period of time. The assembly also has an end cap film covering the fluid outlet.

The presenting invention further provides a medical fluids delivery assembly. The assembly has a container for storing a therapeutic fluid and a laser-weldable tubing. The tubing has a sidewall having a layer of a non-PVC containing polymer blend of a first component of a material not thermally responsive to a laser beam and selected from the group consisting of polyolefins, ethylene and lower alkyl acrylate copolymers, ethylene and lower alkyl substituted alkyl acrylate copolymers, ethylene vinyl acetate copolymers, polybutadienes, polyesters, polyamides, and styrene and hydrocarbon copolymers. The blend has a second component of a laser responsive material having low solubility in aqueous medium and the layer being sufficiently thermally responsive to exposure to a laser beam having a wavelength within a range of wavelengths from about 700 nm to about 1500 nm to melt a portion of the sidewall upon exposure to the laser beam for a short period of time. The laser-weldable tubing being connected to the container.

The present invention further provides a tubing assembly. The assembly has a first tubing, a second tubing and a coupler connecting the first and second tubings. The first tubing is of a first material containing polyvinyl chloride. The second tubing is of a second material which does not bond well directly to the first tubing, the second material of a polymer blend of a first component of a material not thermally responsive to laser beam and selected from the group consisting of polyolefins, ethylene and lower alkyl acrylate copolymers, ethylene and lower alkyl substituted alkyl acrylate copolymers, ethylene vinyl acetate copolymers, polybutadienes, polyesters, polyamides, and styrene and hydrocarbon copolymers, a second component of a laser responsive material having low solubility in aqueous medium and the layer being sufficiently thermally responsive to exposure to a laser beam having a wavelength within a range of wavelengths from about 700 nm to about 1500 nm to melt upon exposure to the laser beam for a short period of time.

The present invention further provides a medical fluid delivery tubing set assembly. The assembly has a first tubing, a second tubing, a third tubing and a coupler. The first tubing is in fluid communication with a source of a therapeutic fluid. The second tubing is of a non-PVC material having a layer of a blend of a first component of a material not thermally responsive to a laser beam and a second component of a laser responsive material. The third tubing is in fluid communication with a patient to be treated by the therapeutic fluid. The third tubing is connected to a first end of the second tubing. The coupler connects a second end of the first tubing to the second tubing.

BRIEF DESCRIPTION OF THE FIGURES

FIGS. 11a, 11b and 11c are respectively cross-sectional views of a monolayer, non-PVC, laser weldable tubing and a multiple layer tubing having the monolayer tubing as a layer therein and a multilumen tubing.

FIG. 12 is a cross-sectional view of a capped tubing assembly.

FIG. 13 is a cross-sectional view of a coupler.

FIG. 14 is a cross-sectional view of a tubing and coupler assembly.

FIG. 15 is a plan view of a medical fluids container connected to a non-PVC laser-weldable tubing.

FIG. 16 is a cross-sectional view of a laser-weldable tubing connected through a coupler device to a tubing from a transfer set.

DETAILED DESCRIPTION OF THE INVENTION

Although the present invention can be made in many different forms, the presently preferred embodiments are described in this disclosure and shown in the attached drawings. This disclosure exemplifies the principles of the present invention and does not limit the broad aspects of the invention only to the illustrated embodiments.

Generally, the present invention relates to the aseptic connection and disconnection of tubing. Such tubing can be advantageously used to transfer fluid or blood to and from the human body. In a preferred embodiment, the present invention pertains to a device that opens sealed tube ends and connects the opened tube ends together. Moreover, the device disconnects a tube and reseals the tubing. All of these processes use laser generated heat and provide a connection or disconnection that is aseptic or sterile.

The Device

Figure 1:
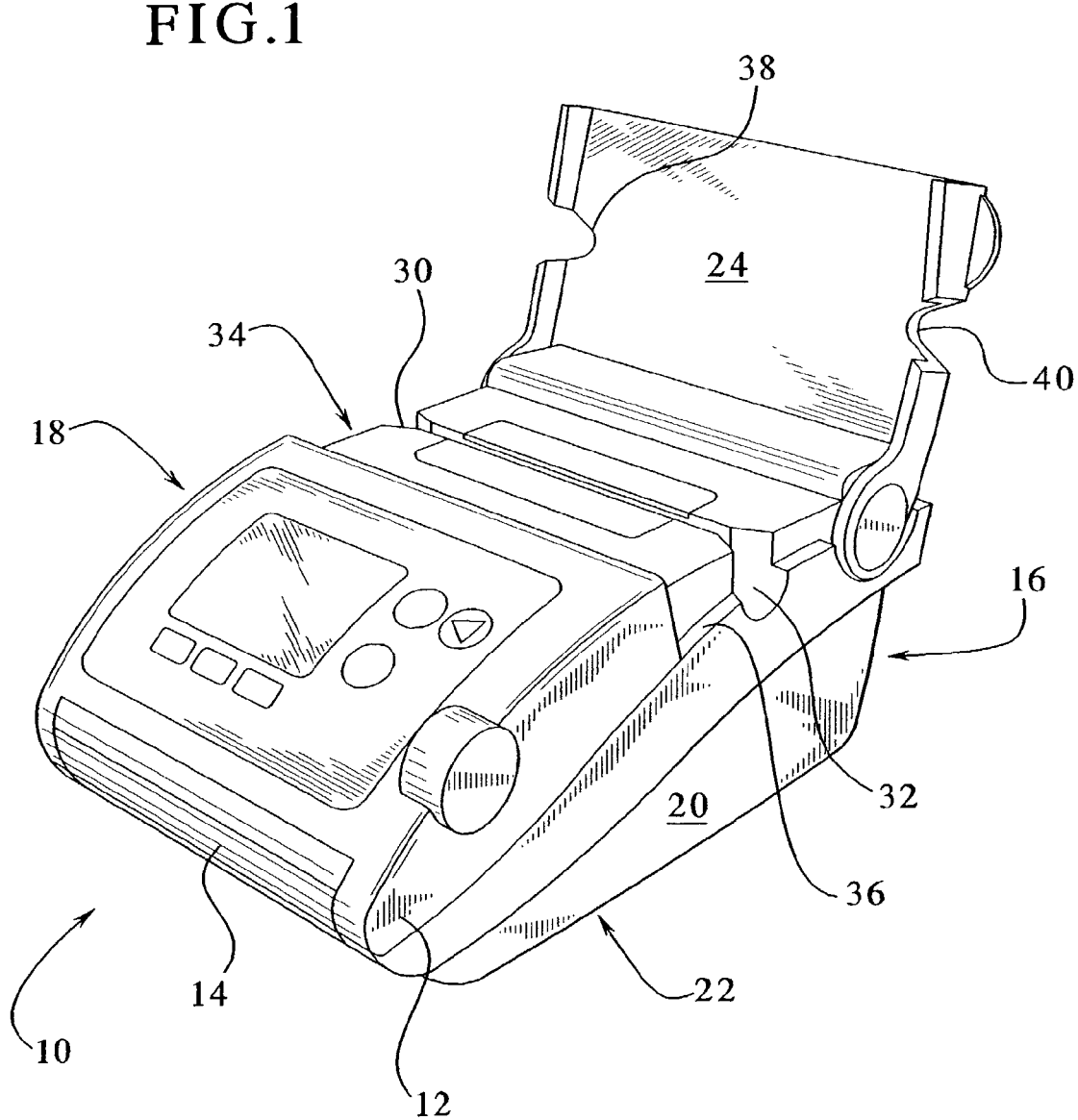
FIG. 1 is a perspective view of a housing of an embodiment of the present invention.

FIG. 1 shows a device 10 according to an embodiment of the present invention. The device 10 includes a housing 12 that has a front 14, a back 16, and two sides 18, 20 there between. The housing 12 also includes a bottom 22 and a lid or door 24. The four sides 14, 16, 18, 20 and bottom 22 define an interior area A. Two slots or openings 30, 32 are located at upper ends 34, 36 of two sides 18, 20 of the housing 12. The door 24 is hinged to the back 16 of the housing 12. The door 24 may be hinged in any number of ways to allow it to be easily opened and shut. The door includes a locking mechanism (not shown) to lock the door closed when the device is in operation. In an embodiment, the door 24 also has two slots 38, 40 that align with the slots 30, 32 to create an area (not shown) for loading and unloading tubing 50 which will be described in further detail below.

FIGS. 2A through 2D show the inside of the device 10 according to an embodiment of the present invention. Inside the housing 12 are two passageways 52, 54. In an embodiment, the passageways 52, 54 are funneled. Each passageway leads to a guide 56, 58. The guides 56, 58 receive the tubing 50 and advance the tubing 50 within the housing 12. The guides are, preferably, pinch rollers, however, various types of guides or threading devices, may be used. In a preferred embodiment, the guides 56, 58 crimp the tubing 50 as it is fed into the device 10. (See FIG. 2A, Ref. No. 58). This crimping purges fluid from a portion 60 of the tube 50 that progresses past the guides 56, 58 into the device.

FIGS. 2A through 2D also show a pair of tube holders 70, 72 aligned with guides 56, 58 in the housing 12. FIG. 3A and 3B show an enlarged view of another tube holder 70 of the present invention. As shown in FIGS. 2A through 2D and 3A and 3B, each tube holder 70, 72 has a first part 74, 76 and a second part 78, 80, respectively. Each first and second part 74, 76 and 78, 80 has a recess or groove 82, 84 that corresponds with an outer diameter B of the tubing 50. The first part 74, 78 is movably attached to the second part 76, 80 via a hinge 85 or similar mechanism. When the tube holders 70, 72 are in the closed position, an aperture 90 is formed extending through the holder 70, 72. A diameter C of this aperture 90 is slightly smaller than the outer diameter B of the tube 50. In this way, the tubing 50 is fed through the guides 56, 58 and received in the tube holders 70, 72. In an embodiment, an inside surface of the tube holders 70, 72 is tapered (not shown). The aperture 90 may be slightly tapered toward the center of the device 10. In this example, the diameter C of the aperture 90 facing the inside of the device is smaller than a diameter of the aperture facing the guides 70, 72. When in the closed position, the tube holders 70, 72 close with sufficient force to grip, but not flatten, the tubing. In addition, if necessary, the aperture 90 uniformly compresses the tubing 50 and forces the tubing to maintain a cylindrical shape. This may be necessary if, for example, the tubing 50 is not cylindrical due to storage conditions of the tubing or prior sterilization methods, e.g., steam sterilization or ETO sterilization, which may cause the tubing 50 to coil and not be perfectly round.

In an embodiment, the tube holders 70, 72 are mounted on a bar 100. Each tube holder has a guide arm 102, 104 associated with it. The guide arms 102, 104 extend below the bar 100 to a track 105 in a plate 106. As described in more detail below in conjunction with FIGS. 4A through 4H, the plate 106 moves back and forth within the housing 12. As the plate 106 moves to the back 16, the tube holders 70, 72 move in a straight line toward each other to the center of the device 10 (See FIGS. 4D and 4E). The guide arms 102, 104 may be, for example, a lead screw or lever/cam/slot mechanism or a combination of any of these. With the assistance of the guide arms 102, 104, the tube holders 70, 72 pull or push the tube 50 within the housing 12; thus, manipulating the tubing 50 to a desired position, e.g., sterilizing and opening two sealed ends of tubing, and connecting the two ends together, or disconnecting, sterilizing and sealing the ends of a single tube.

As will be described in detail below, the device 10 also includes a hammer 110 and an anvil 112. The hammer 110 and anvil 112 are used during the disconnecting process of the tubing 50. The hammer 110 is movably mounted to a motor 114 via a shaft 116. In an embodiment, the hammer 110 moves forward and backward along the shaft 116 in the housing. As the hammer moves forward, a front part 111 of the hammer contacts a surface 113 of the anvil 112. The hammer 110 may be made from a metal, ceramic, or even rigid plastic material.

Laser Optics

The device also includes a laser unit 200. In a preferred embodiment, the laser unit 200 is a semiconductor diode laser which can be a single laser diode or a laser array of diodes. However, other types of lasers can be used in the invention. For example, Argon, $CO_2$ or YAG lasers may be used. The laser characteristics, e.g., wavelength of the laser, should be evaluated to determine the corresponding characteristics of the tubing 50 to be used in the application. In an embodiment, the laser unit 200 may have an optical assembly to direct a controlled laser beam to the desired location for the connecting or disconnecting processes.

FIGS. 2A through 2D and 4A through 4H show an optical assembly 202 according to an embodiment of the invention. In this example, the optical assembly 202 includes a collimator 204, and a reflective prism 206. Depending on the characteristics of the laser unit 200, a laser beam may begin to diverge as soon as it leaves the unit 200. In this scenario, the collimator 204 limits the divergence of the laser beam. Specifically, the collimator 204 has a generally flat back surface 207 that faces the laser 200. The collimator 204 also has slightly convex front surface 208. As the laser energy travels through the collimator 204, the collimator refocuses the laser beam to the prism 206. Other applications, for example $CO_2$, may have a small laser beam that can be expanded by using a beam expander. The collimator 204 is, preferably, made from an acrylic material, however, other transparent or translucent materials may be used.

The prism 206 splits the laser beam and directs the split beam to the desired location, e.g., the tube ends 51, for the connection process. In order to obtain optimal laser concentration during the connection process, the design of the prism 206 is directly related to the prism location in the device 10. In a preferred embodiment, the prism 206 is between the two tube holders 70, 72. In this example, the prism 206 is constructed from two plano convex lenses 210, 212 juxtaposed to each other.

As is further described below, the prism 206 may also include a light pipe 220 that intersects a center 222 of the prism 206. The light pipe 220 directs the laser beam during both the connecting and disconnecting processes. In addition, the anvil 112 is along a back 224 of the prism lens 206 and, specifically, near an end 230 of the light pipe 220.

Tubing

In general, the material of the tubing 50 is a flexible plastic. The tubing and assemblies thereof are discussed in greater detail below. In a preferred embodiment, the material is a thermoplastic, kraton polypropylene blend, or the like. In one preferred form of the invention a chemical additive is added that is responsive to the laser to generate heat. One particularly suitable additive can be selected from dyes. The dye is selected to absorb energy at or near the wavelength of the laser diode to promote absorption of the energy of the laser, thereby heating the tubing. Thus, the frequency of the laser selected, e.g., semiconductor diode or YAG laser, should match the specific characteristics of the dye that is added to the tube material. In some applications, e.g., $CO_2$ laser applications, no dye may be required because the absorption wavelength of the tube is the same as the wavelength generated by the laser.

Moreover, a second dye may be added to color code each of the tubes. Such color coding creates a machine detectable and patient detectable distinction between the tubing that is connected to the patient and the new tubing to be connected. For example, the catheter tubing that is implanted in the patient, or the transfer set connected to the catheter, may be dyed one color and the tubing that is attached to the bag of fluid may be dyed a different color. This color distinction is especially helpful for patients that are visually impaired. Other methods of distinction may be employed without departing from the spirit of the invention.

Sensors

A number of sensors 300, 302, 304, . . . are positioned within the housing 12. It should be understood that the location of the sensors identified in the drawings is just one example. Other acceptable locations for the sensors may be accomplished depending on the layout of the components within the device 10. These sensors detect and confirm different stages of the process, whether it is during the connection or the disconnection processes. For example, during the connection process, a sensor 300 may be employed to identify an object at the funneled pathway 52, 54. If the object is acceptable, e.g., the tubing 50, the sensor 300 will activate the guides 56, 58. If the object is not acceptable, the guides are not activated. Thus, these sensors help to keep out foreign objects, and even fingers. This sensor 300 may be, for example, an absorption sensor. An absorption sensor identifies tubing 50 that has a dye. In this way, not only will the sensor keep out foreign objects but also it will identify if improper tubing is attempting to be loaded. As mentioned above, the patient's catheter (or transfer set connected to the catheter) may be a different color than the tube connected to the fluid or blood to be administered to the patient. In this way, the absorption sensor checks to make sure the patient-side and disposable (or bag-side) sealed end tubes are loaded in the pathways 52, 54. If the user attempts to improperly load two bag-side tubes, the sensor 300 alerts the user and the user must retry the loading procedure. Depending on the application, the sensor may be set to allow certain combinations of tubing to enter the apparatus. Thus, the sensor 300 provides a safety measure to guard against improper loading.

Another sensor that may be used in the device 10 is an edge sensor 302. The edge sensor 302 identifies when tube ends 51 extend beyond the tube holders 70, 72 during loading of the tube ends 51 into the device. Specifically, as the tube end 51 crosses the light beam path, the signal from the photo detector 302 is fed into a comparator. The sensor 302 subsequently switches the output state at the desired threshold level, e.g., when sufficient tube length extends beyond the tube holder 70, 72. The sensor 302 may be, for example, a precision edge sensor such as a Cartesian Ovoid LED and a die mounted aperture photo detector. However, other sensing devices capable of identifying the edge of the tube 50 may be used.

Moreover, during the disconnection process, the single tube is loaded into the device for sealing and separation. A color sensor 300 or 304 checks to make sure that not all the tubing in the device is the same color. If the entire tube 50 is the same color, the device will not be able to locate the prior weld. The sensor 304 alerts the user and the patient must reload the tube 50 and try again. This occurs because the sensor 304 also determines where to disconnect the tube 50 based on the position of an existing weld W in the tube. Therefore, when two tubes of different color are present at the sensors 304 the existing weld W is somewhere in between.

After the sensors confirm the tubing 50 is loaded properly, the same or different sensor 304 determines the location of the existing weld W in the tube. This may be accomplished, for example, using a digital camera—like mechanism that searches for the flange in the weld. In a preferred embodiment, the sensor 304 is a CMOS Image Detector. Once the existing weld W is located, the sensor identifies the position for crimping, sealing and separating the tube. The sensor then activates the guides and moves the tube a predetermined distance, on the catheter side, toward the patient. For example, the existing weld may be located at position X. The sensor locates the weld and moves the tube X+⅛" toward the patient side for the location of the cut. In this way, the sensor ensures that the section of tube containing the existing weld W is discarded. This maintains the integrity of the remaining tube in the transfer set that leads to the catheter tube implanted in the patient. In addition, the sensor provides a safety measure since making a new weld on top of an existing weld may not be sufficiently durable.

Alternatively, the sensor 304 may detect a distinction in color between the tubing based on a color coding scheme like that described above. Accordingly, the sensor identifies a color change at the area surrounding the weld.

As described in further detail below, the device 10 also includes a number of temperature or heat sensors (320) to maintain consistency throughout the operation of the device. These sensors 320 may be infrared sensors, such as thermopile infrared sensors. However, other sensors such as thermal couplers or thermistors may be employed. The sensors 320 are used, for example, during the connection and disconnection processes. The sensors verify the tubing is heating properly and may be calibrated to indicate a level of heat is reached for a "good weld" or "bad weld." For example, in applications where the tubing includes a dye, the heat is absorbed by the dye and, in turn, the tubing begins to melt and flow. In this way, the sensors are non-contact temperature sensors that correspond to the infrared output of the tubing as the tubing absorbs the energy from the laser.

Thus, sensors may be employed to compensate the effectiveness of the system based on efficiency of the dye concentration of the tubing, power variation, or laser optic variations.

The Method

Figure 2A:
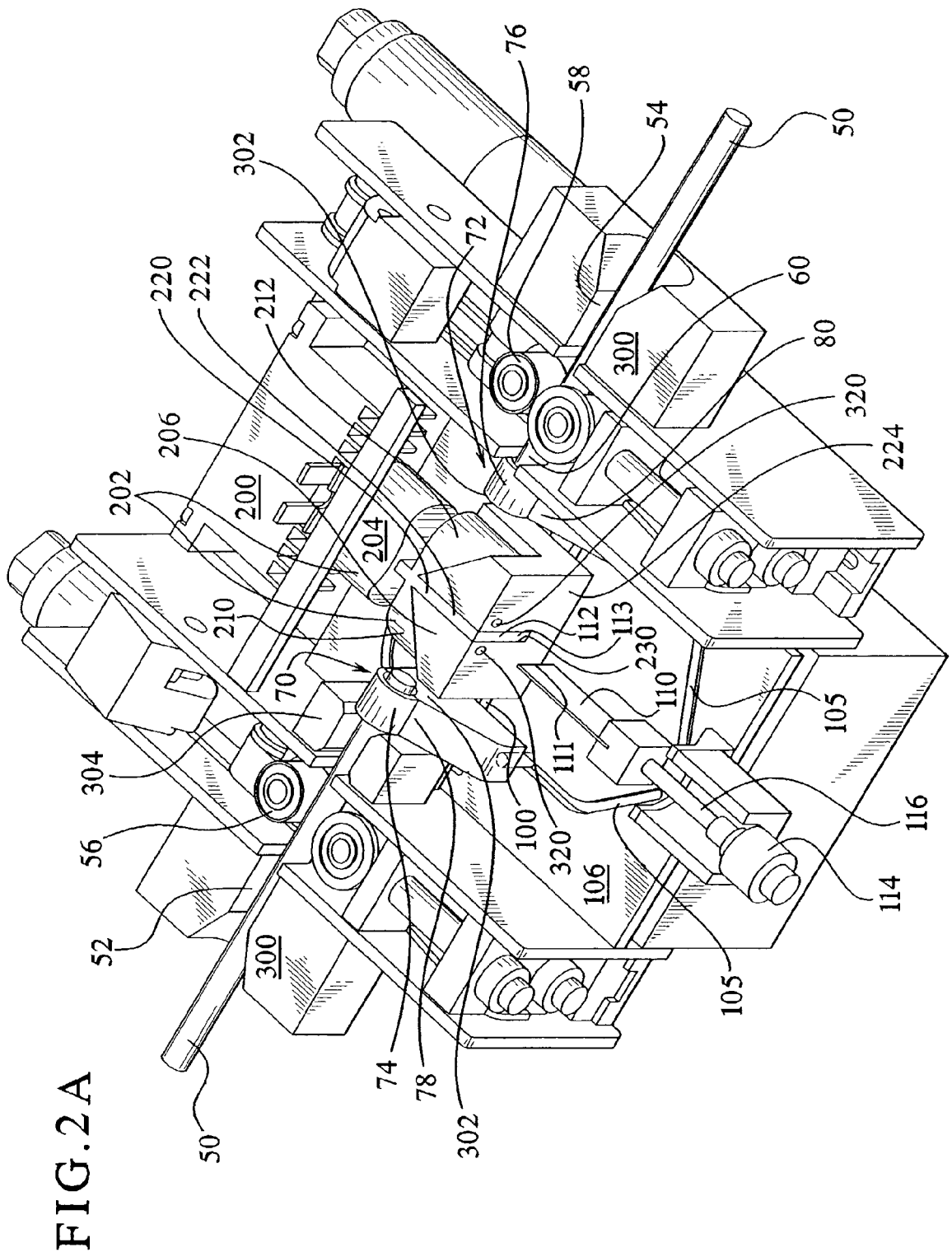
FIGS. 2A through 2D are perspective views of a connection and disconnection device according to principles of the present invention.
Figure 2B:
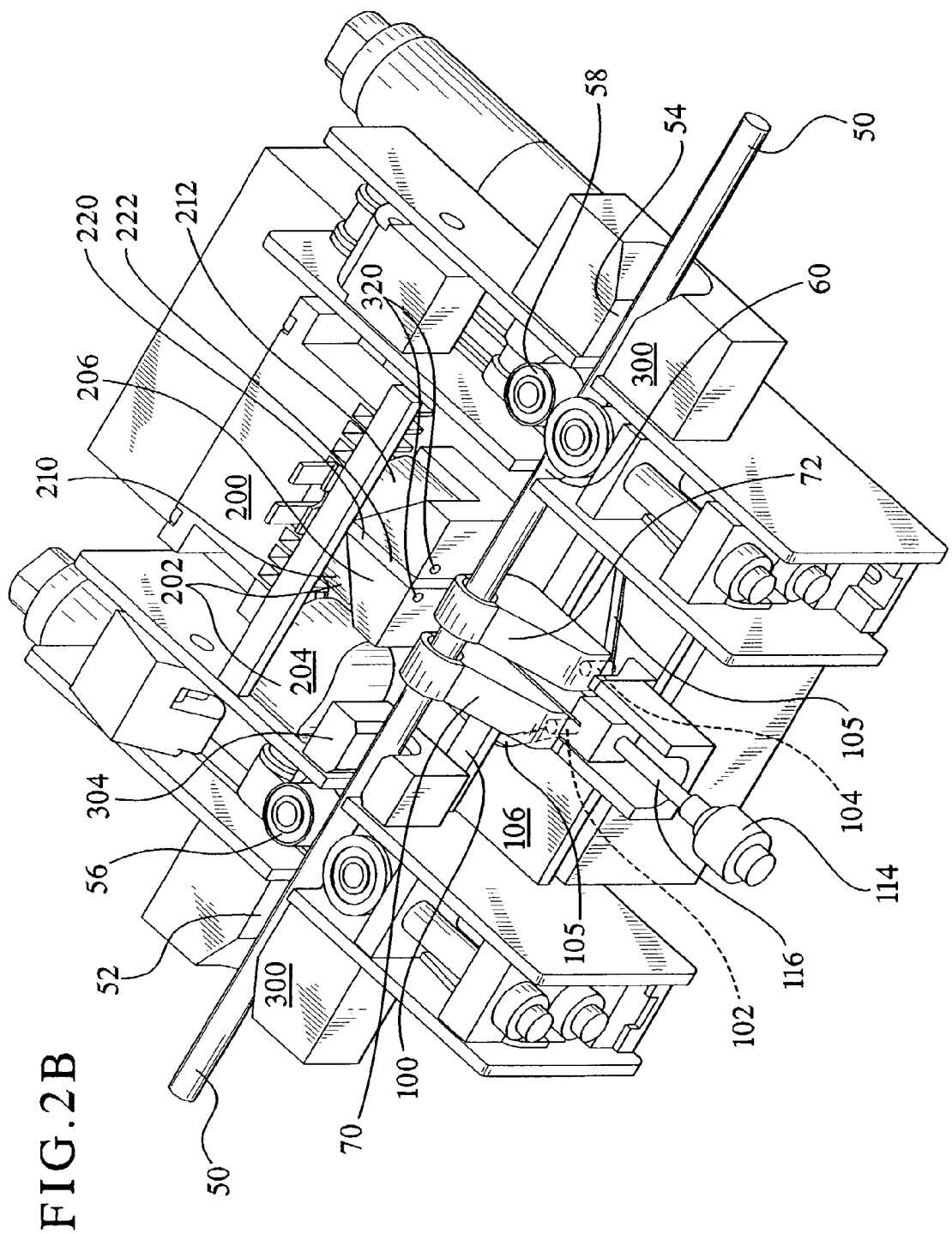
Figure 2C:
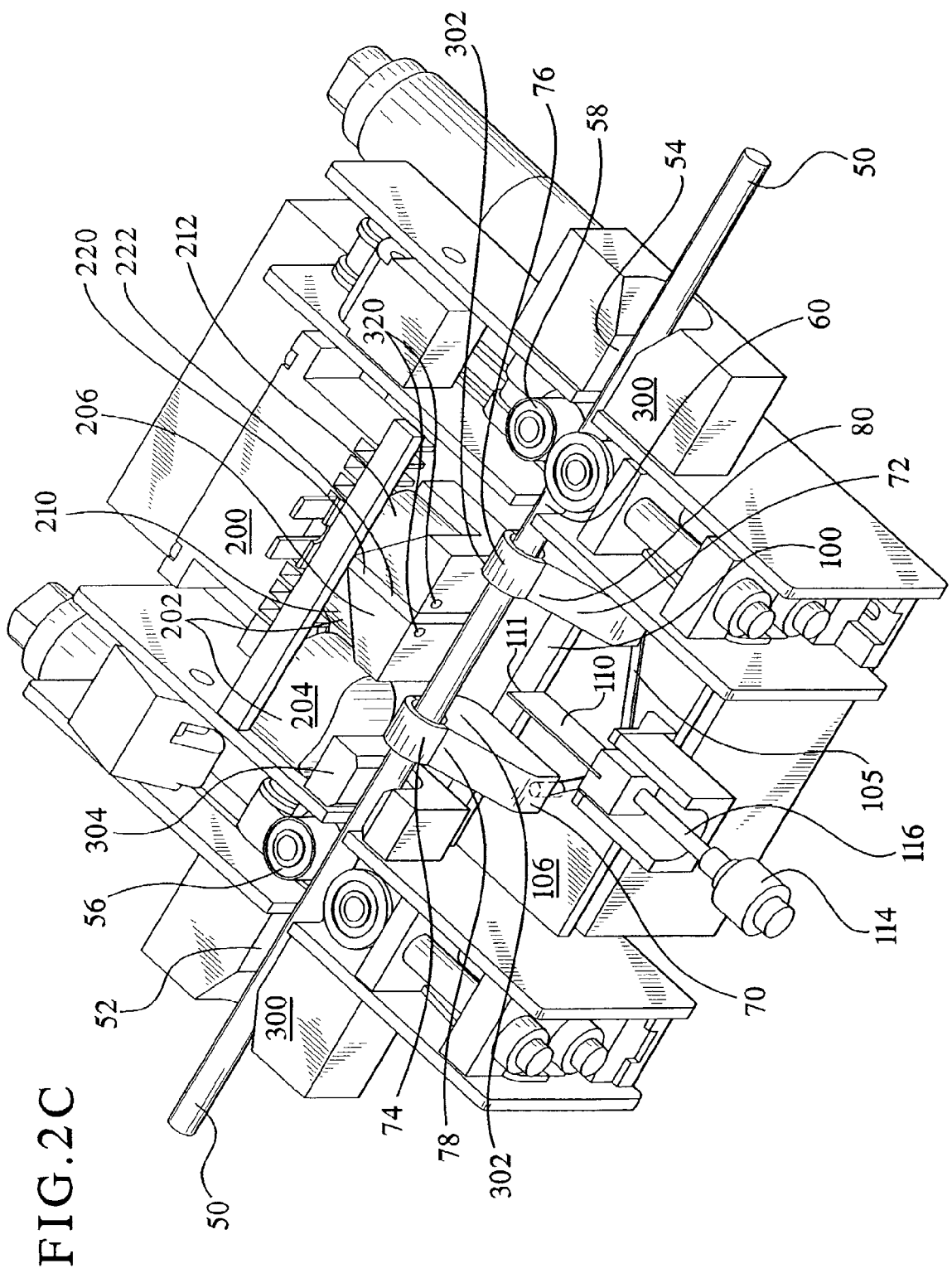
Figure 2D:
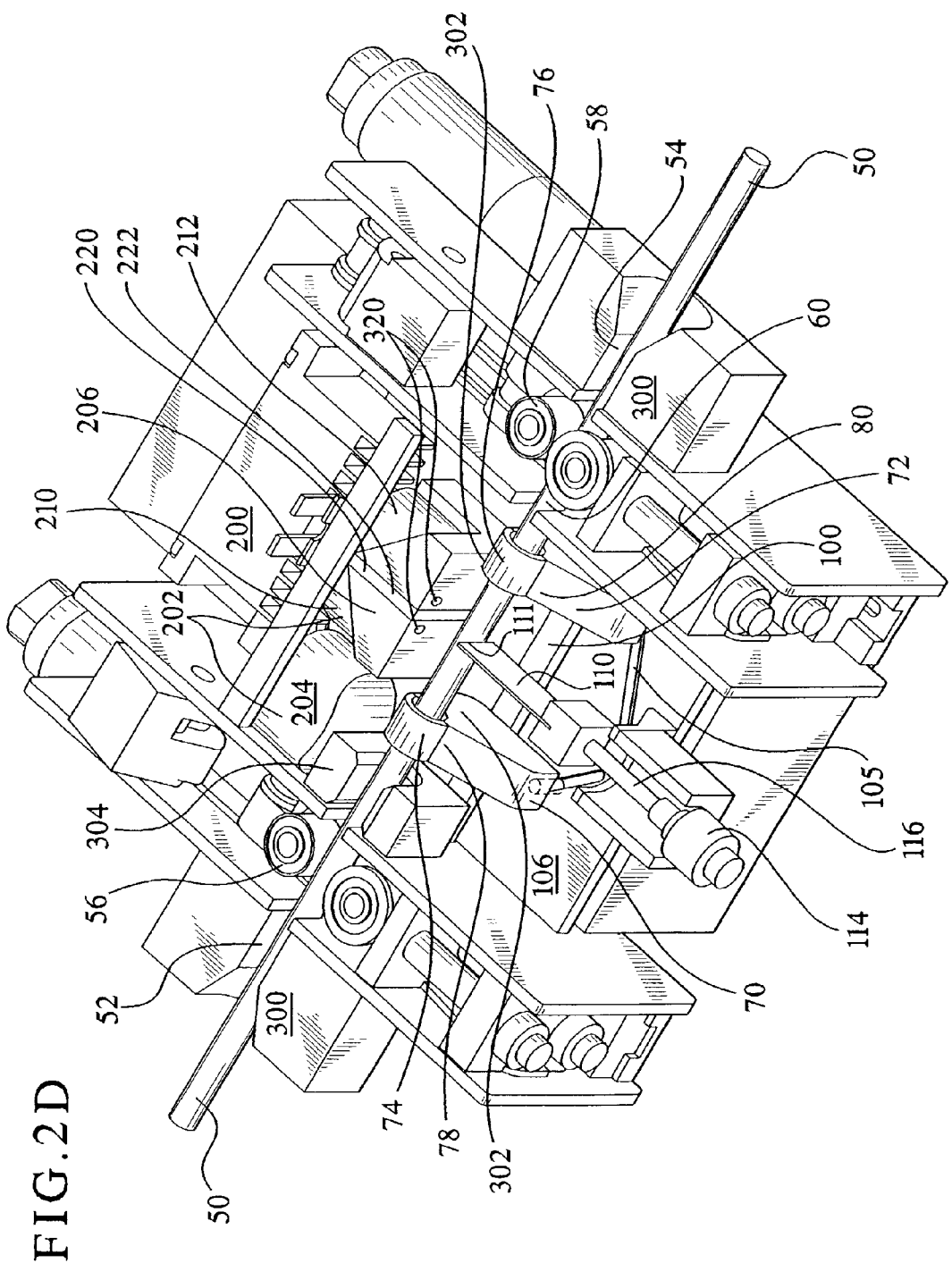
Figure 3A:
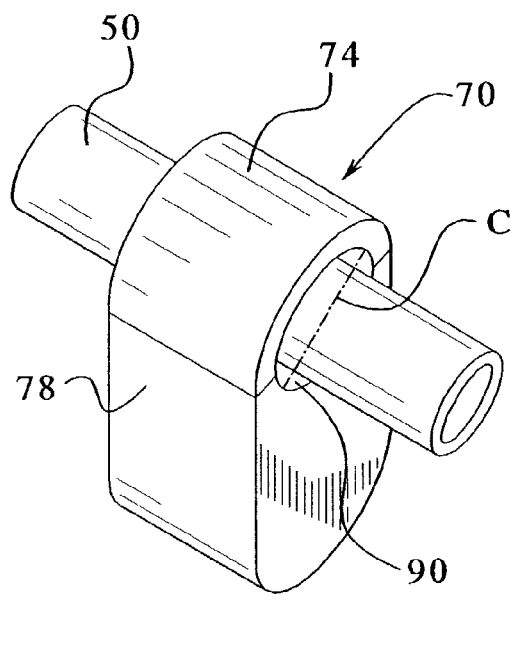
FIGS. 3A and 3B are perspective views of another tube holder of an embodiment of the present invention.
Figure 3B:
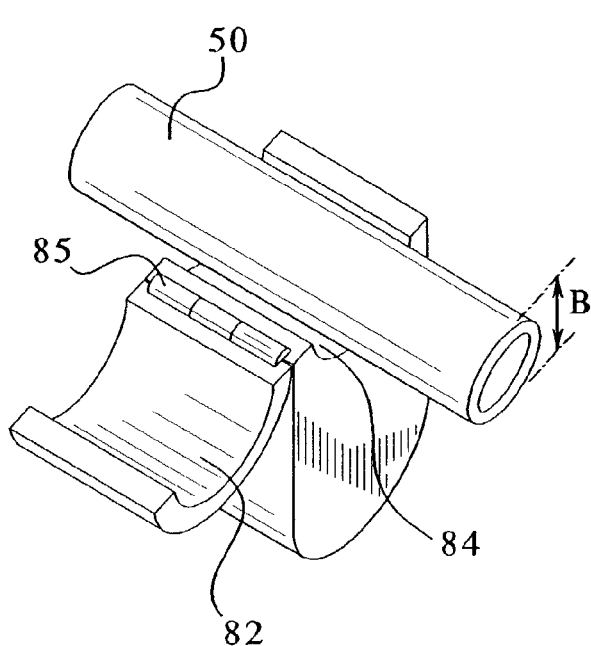

FIGS. 2A through 2D illustrate the connecting and disconnecting process as follows. Specifically, FIGS. 2A and 2B show the inventive process that connects two tube ends together. FIGS. 2C and 2D show the inventive process that disconnects the tubing. Additionally, FIGS. 4A through 4H show a simplified schematic of the connecting process.

Method of Connecting Two Tube Ends

Figure 4A:
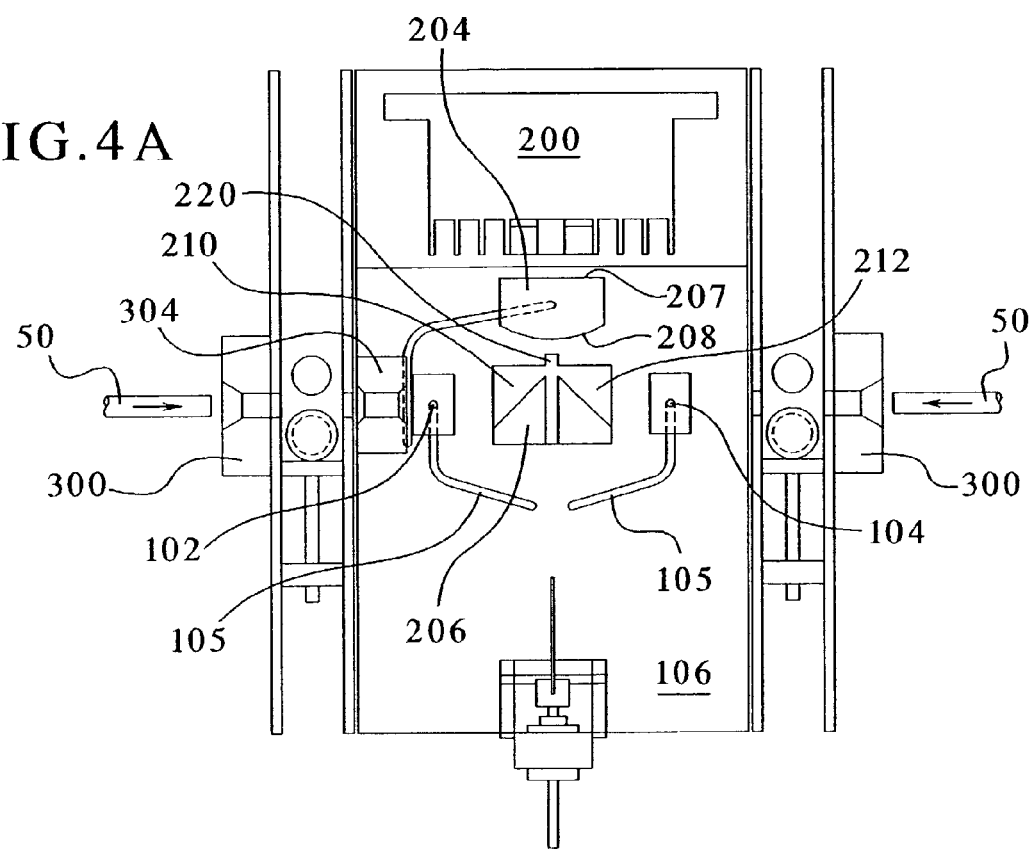
FIGS. 4A through 4H are schematic plan views of the device embodiment in FIGS. 2A through 2D.

The method of connecting two tube ends will now be described. During the connection process, the lid 24 is closed. As shown in FIGS. 2A and 4A, the user inserts two tubes 50, each having a sealed end 51, into the device 10 via the loading area openings 30, 32, 38, 40. However, it is within the scope of the invention to use at least one tube end 51 that is not sealed, but, open. In applications involving an open tube end, several types of end caps may be used to maintain the necessary sanitation levels at the inside of the tube. One type of end cap may be a sealed "drum head" that covers the end of the tube. The sealed "drum head" may be a piece of film placed over the open end of the tube and sealed around the entire face of the tube. Another example may include an open end with a vented seal over the face of the tube. A vented seal may be, for example, a perforated membrane. In this example, an end cap would be added to cover the vented end for sanitation purposes. The tubing and cap assembly will be discussed in greater detail below.

Figure 4B:
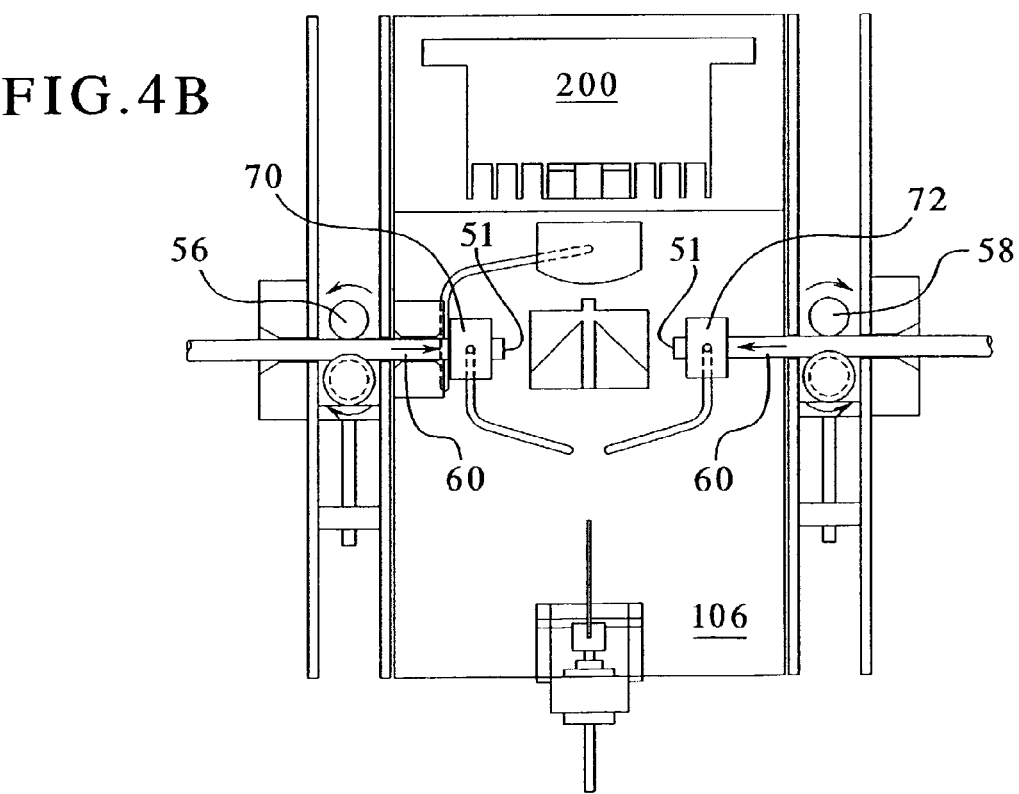

As each tube end 51 enters a respective passageway 52, 54 the sensor 300 identifies the tubing 50 and checks to make sure that one tube end 51 is the patient's tube and the other tube end 51 is the bag tube. It should be noted that it does not matter which tube is loaded into which loading area. Advantageously, the sensors 300 at the passageway 52, 54 communicate with each other to determine that one of each tubing type is loaded. When the tubing is properly loaded, the guides 56, 58 are activated. (FIG. 4B). The guides 56, 58 crimp or squish the tubing and advance each tube end 51 into the device 10 to the tube holders 70, 72. This crimping or squishing creates a vacuum effect in the tubing and purges fluid from the portion 60 of tubing that enters the device 10. The precision edge sensor 302 identifies when the tube 51 extends the predetermined length beyond the holder 70, 72 and stops the guides 56, 58.

Figure 4C:
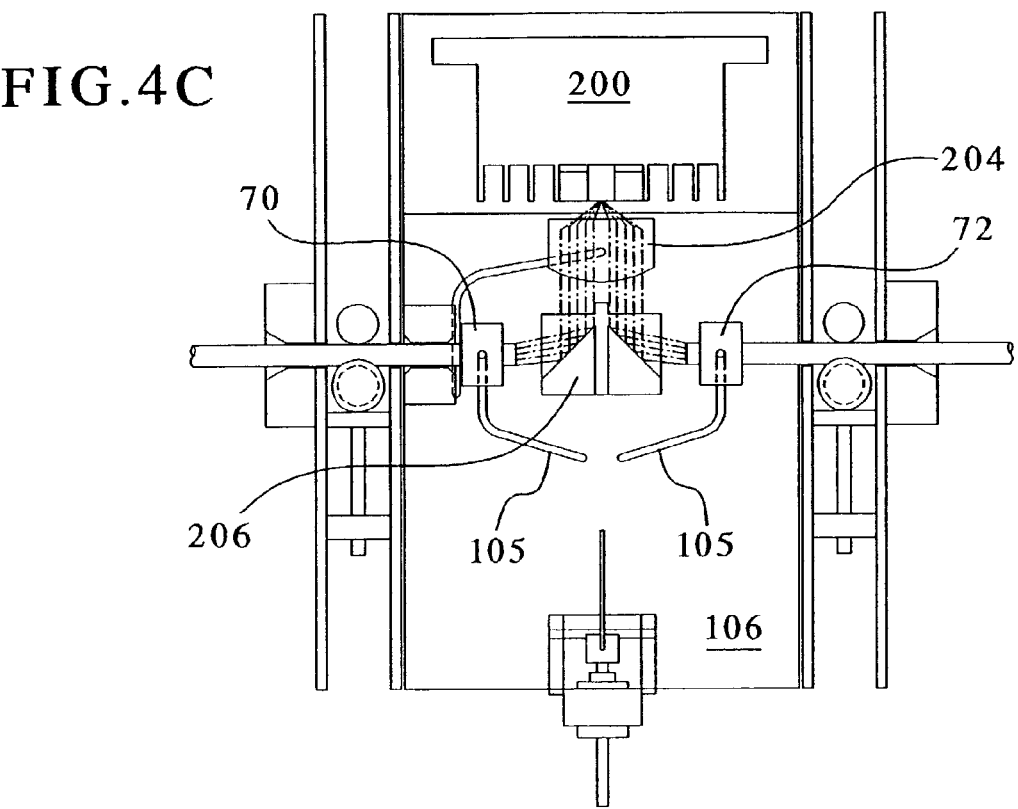

In FIG. 4C, the reflective prism 206 is between the tube holders 70, 72. After each tube end 51 is loaded into its respective tube holder 70, 72, the laser unit 200 is activated and energy diverges from the laser source. The collimator 204 refocuses the diverging energy toward the prism lens 206. As the energy/light strikes the reflective prism 206 it reflects into two bundles of energy. In this embodiment, the prism lenses 210, 212 re-direct each bundle of energy at approximately a 90° angle to focus the energy around the tube ends 51. More particularly, a "spot" of energy strikes the tube ends 51 and preferably, slightly exceeds the diameter B of the tube 50 to ensure the tube is covered with adequate radiant energy.

Heat sensors 320 positioned in the housing 12 detect the temperature near the sealed ends 51. Such heat sensors 320 may be, for example, thermopile infrared sensors. As the laser beam strikes the sealed tube ends 51, the heating, melting and aseptic (and/or sterilization) process begins. Depending on the application, the sensors can be used to detect the desired temperature levels for melting and welding. For example, some applications require aseptic conditions be generated. Typically, aseptic, high level disinfection, or germicidal conditions include a less than 6 log reduction of heat resistant spores. Other applications may require sterile conditions be generated. Sterile conditions generally include an operating mode of equal to or greater than a 6 log reduction of heat resistant spores.

Figure 5A:
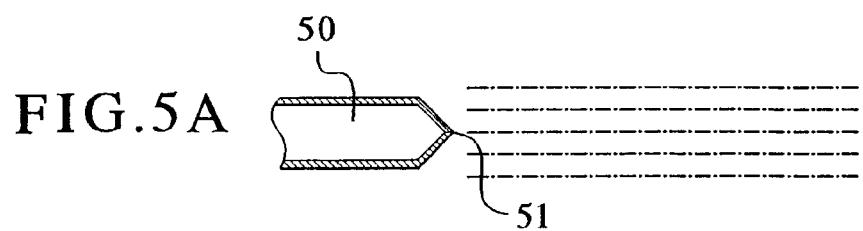
FIGS. 5A through 5C are schematic cross-sectional views of an embodiment of a sealed end tube of the present invention.
Figure 5B:
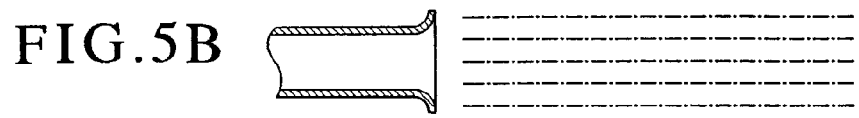

As the temperature of the tubing material at the tube ends 51 increases, the tube ends 51 begin to melt, flow and reopen. The tubing material has a certain level of "memory"—as the sealed end of the tube reopens, the tube is predisposed to returning to its symmetrical, circular form. FIGS. 5A and 5B illustrate an example of the laser beam striking the sealed tube end 51. As the laser beam strikes the tube end the rise in temperature at the tube end causes the sealed end to peel open and flare. Once the heat sensors 320 detect that the required aseptic or sterilization temperature level is obtained and sufficient melting of the tube ends 51 has occurred the laser 200 shuts off.

Figure 4D:
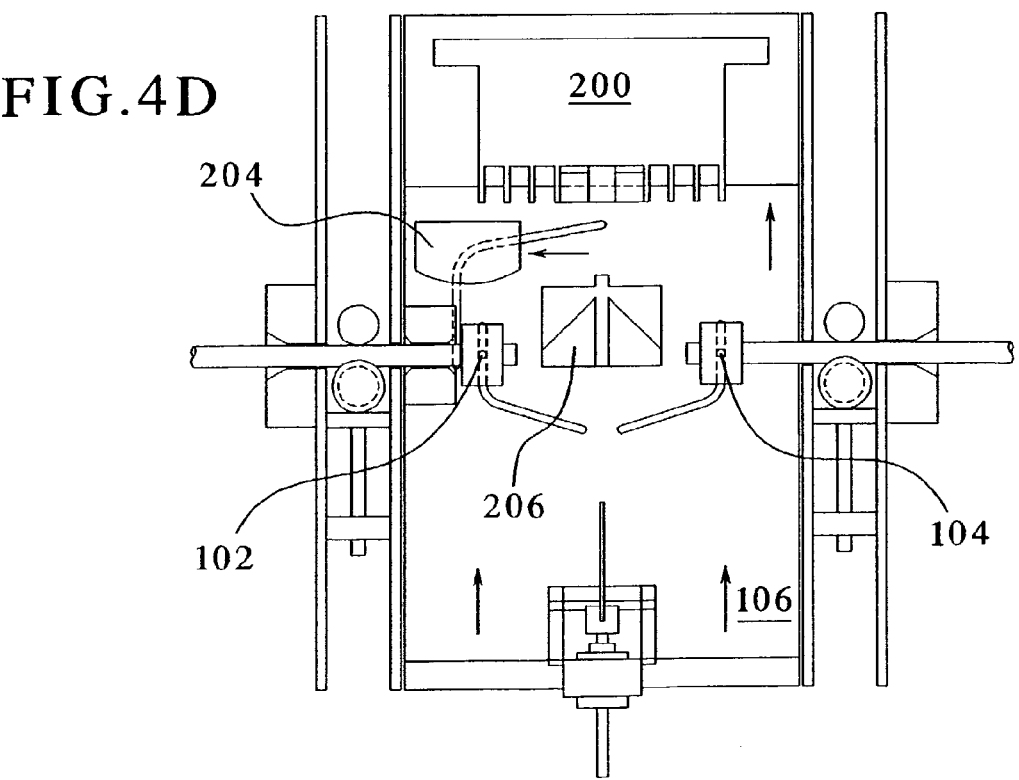
Figure 4E:
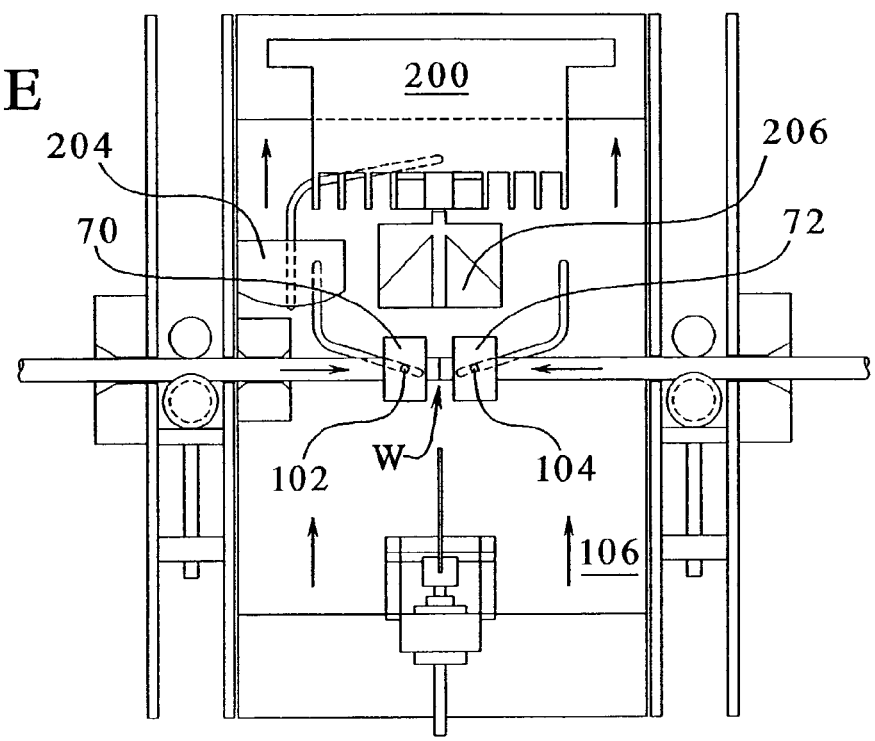
Figure 4F:
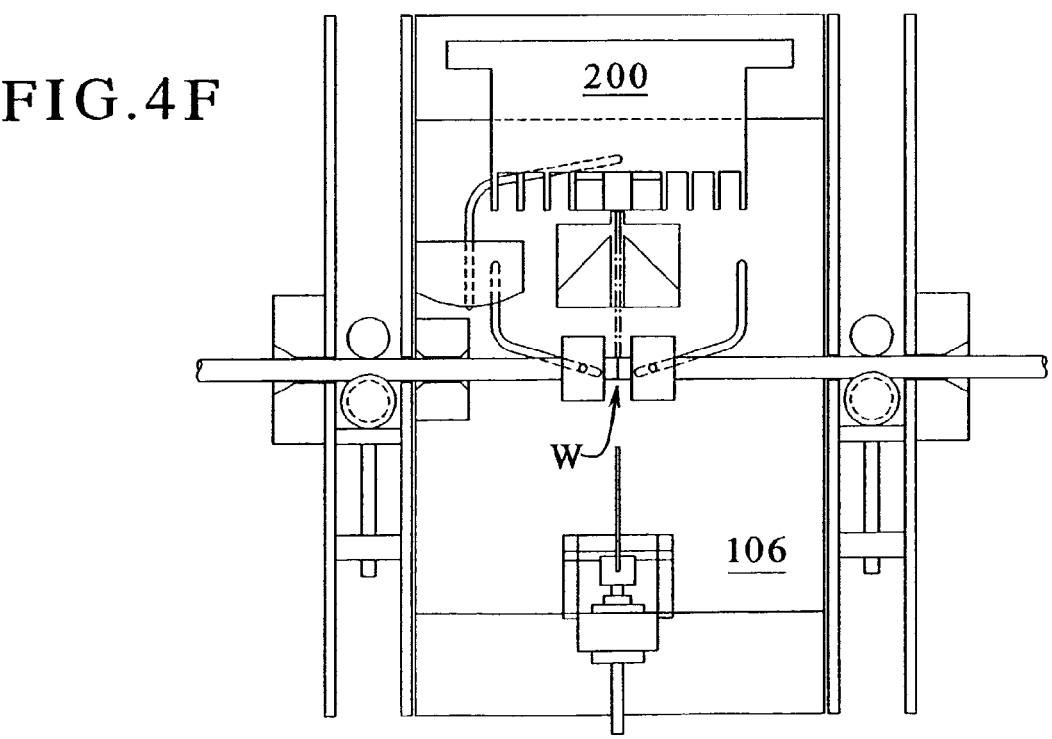
Figure 5C:
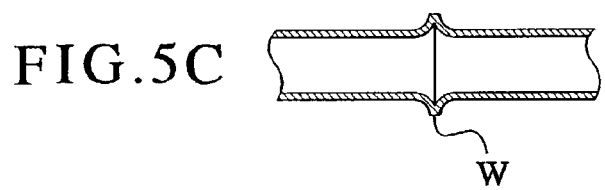

FIGS. 4D through 4F show the next step of the connecting process. After the laser 200 shuts off, the plate 106 moves to the back 16 of the housing 12. As the plate 106 moves, the collimator 204 moves to the side 18 along track 107. At the same time, the prism 206 moves toward the laser unit 200, and the tube holders 70, 72 come together via track 105. At this point, the now melted and aseptically heated or sterilized tube ends 51 contact each other. A weld-seal W is formed. Typically, the weld W is in the form of a ring as shown in FIG. 5C. The tube holders 70, 72 remain in this position until the weld W has sufficiently cooled. In another embodiment, the laser unit 200 may be energized again (FIG. 4F). As shown in FIG. 4F, the laser beam is directed down the light pipe 220 to the tube ends. In this example, the weld-seal W forms and the laser unit 200 is shut off. In an embodiment, the weld-seal W is a hermetic seal.

In applications that use at least one "drum head" end, this type of end responds to the laser in a similar manner as that described above regarding the opening of a sealed end tube. One example of the "drum head" end is as follows. The film of the "drum head" may have a higher concentration of dye than the tubing material. Thus, the film heats faster than the tubing material. The film melts and flows outward to the perimeter of the tube and combines with the tube. The film material may be made from a variety of polymer materials such as polyolefins, polyamides, polyesters, styrene and hydrocarbon copolymers and particularly block copolymers of styrene and dienes and their hydrogenated derivatives, ethylene and vinyl acetate copolymers, ethylene and methacrylic acid copolymers and their ester derivatives. The film may be made from a blend of these materials and can be a monolayer or multiple layer structure. For example, polypropylene, polypropylene-Kraton blend, polypropylene polyethylene blend, or other compatible material.

Other embodiments may include one tube holder that is stationary and one tube holder that moves within the apparatus.

Weld Inspection Process

Figure 4G:
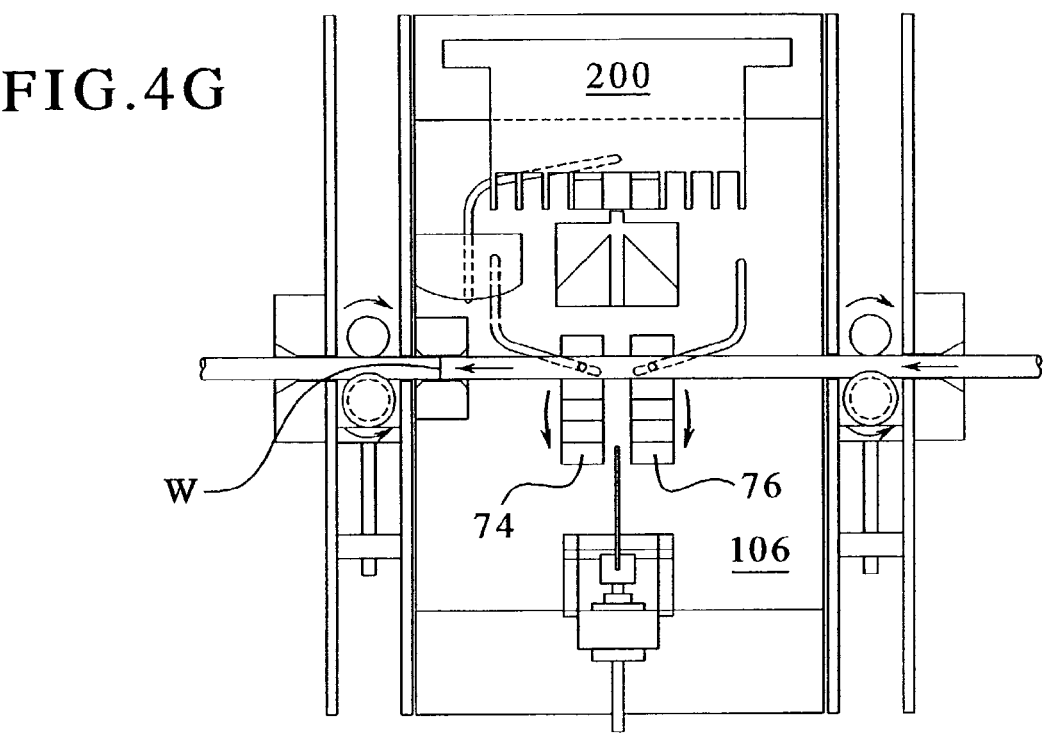
Figure 4H:
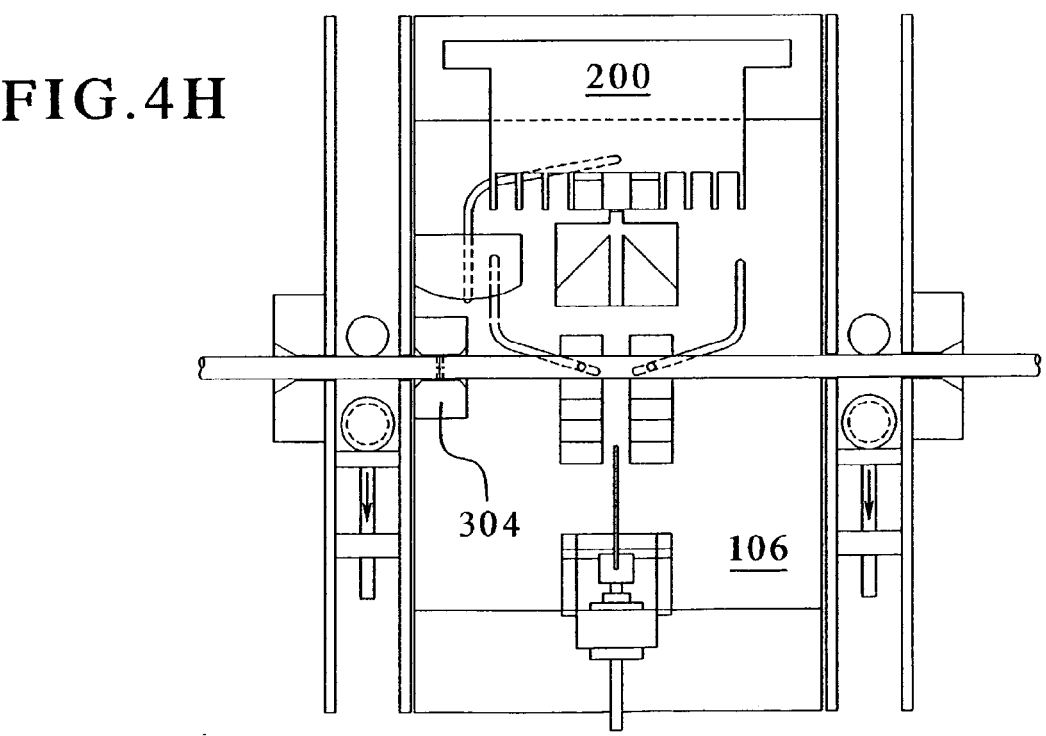

FIGS. 4G and 4H show the weld inspection process. Upon cooling, the first part 74, 78 of the tube holders 70, 72 open and the guides 56, 58 move weld W to the weld detecting sensor 304 for the post process inspection. The inspection process analyzes, for example, the weld thickness and weld height. This data is compared to the profile data for an acceptable or "good" weld. In a preferred embodiment, this sensor 304 is a CMOS image sensor. However, other similar image sensors may be employed. If the post process inspection indicates that the weld is a "good" weld, the lid 24 is unlocked and the guides 56, 58 open. The user is free to open the lid 24 and remove the connected tubing.

On the other hand, if the post inspection process indicates a "bad" weld, the device automatically pinch seals the patient-side of the tubing. The automatic pinch seal process reduces the possibility of contaminants entering the tubing. During this situation, the user is notified of the "bad" weld. The user can then obtain another bag-side tube and start the connection process again. This unique inspection process provides a safety feature to ensure the patient uses "good" welds only. This is especially helpful for visually impaired patients who may have difficulty visually inspecting a weld after the connection process.

Method of Disconnecting a Tube

FIGS. 2C and 2D generally illustrate the inventive method for disconnecting and sealing the tube 50. When the user desires to disconnect from the dialysate solution bag, drainage bag, blood bag, or the like, he/she opens the lid 24 of the device 10. When the lid 24 opens, the guides 56, 58 automatically move to the open position. (FIG. 2C, Ref. No. 56). The user places the tube 50 in the groove of the second part 78, 80 of the tube holders 70, 72. In this way, the tube 50 extends along the funneled passageway 52, 54. In this application, it is not necessary for the first part 74, 78 of the tube holders 70, 72 to close. The user closes the lid 24, thus, closing the guides 56, 58 which, in turn, crimp the tubing 50.

It is preferable to place the tube 50 so that the preexisting weld W is approximately centered between the tube holders 70, 72. Similar to the connecting process, the sensor 300 identifies the tubing 50 and confirms that a patient-side tube is at one of the passageways 52, 54 and the bag-side tube is at the other passageway 52, 54. Thus, the sensor 300 confirms that a preexisting weld exists somewhere there between, e.g., within the device.

After the sensors 300 accept the tubing, the same or different sensor 300 or 304 determines the location of the pre-existing weld W in the tube. This may be accomplished, for example, with a digital camera or similar device. The sensor searches for a flange in the weld W. Alternatively, the sensor 304 may detect a distinction in color between the tubing based on the color coding scheme such as that described above. Accordingly, the sensor 304 could identify a color change at the area surrounding the weld, indicating a weld W exists between the two different colors.

Once the pre-existing weld W is located, the sensor 304 identifies the position for the cut in the tube 50. The guides 56, 58 are activated and the tube 50 moves a predetermined distance, on the catheter side, toward the patient. For example, the existing weld may be located at position X. The sensor 304 locates the weld and moves the tube X+⅛" away from the patient side for the location of the crimping and separation of the tube. In this way, the position for the disconnection is a minimal distance from the existing weld. Therefore, waste of tube material of the patient catheter (or transfer set) is minimized. Alternatively, a patient extension line may be used between the transfer set and the disposable (or bag-side). The use of an extension line will prolong the life of the transfer set because the transfer set will not need to be replaced as often. Instead, the patient extension line is easily replaced by disconnecting the old extension line from the transfer set and connecting a new extension to the transfer set by the methods disclosed herein. Moreover, the sensor 304 ensures that the section of tube containing the existing weld is discarded. This improves the integrity of the remaining catheter tube. In addition, the sensor 304 provides a safety measure since making a weld on top of an existing weld may not be sufficiently durable.

At the start of the disconnecting process the laser unit 200 is off. As shown in FIG. 2D, the hammer 110 moves (via shaft 116) into contact with the tube 50. It should be noted that the hammer 110 is not heated prior to contacting the tube 50. As the hammer 110 contacts the tube 50 it compresses the tube so that the inner surface of the tube is touching. To this extent, the hammer 110 pushes the liquid existing in the tube 50 out of the area to be disconnected.

The laser unit 200 is subsequently activated. The light pipe 220 directs the majority of the laser energy down it onto the tubing 50. The tubing 50 continues to be pinched between the anvil 112 and the hammer 110. In this example, the light pipe 220 is a part of the anvil 112. As the heated tubing is pinched it begins to seal. The heat sensors 320 monitor the temperature near the pinched tubing. The laser unit 200 is shut off. In an embodiment, a sensor 320 is mounted on the hammer 110 near the front 111. In general, the sensor verifies the laser is operating properly. The pinch hammer 110 remains in contact with the tubing while the tube cools. After the cooling of the tubes, the hammer 110 moves back to its original position. The guides 56, 58 are then activated and reverse movement a predetermined distance. This predetermined distance is dependent on the size and material of the flexible tube 50. As the guides 56, 58 reverse, the tubing 50 is pulled apart resulting in two sealed ends. Thus, the combination of the guides 56, 58 and the hammer 110 act as a separator to separate the tubing into two sealed end tubes. The device 10 notifies the user that the lid 24 is unlocked and ready to be opened. The two newly sealed ends of tubing are subsequently unloaded from the device 10. Other applications may include a laser that stays on for the duration or is pulsed on and off while the hammer moves in to pinch the tubing.

Protective Film

Figure 6:
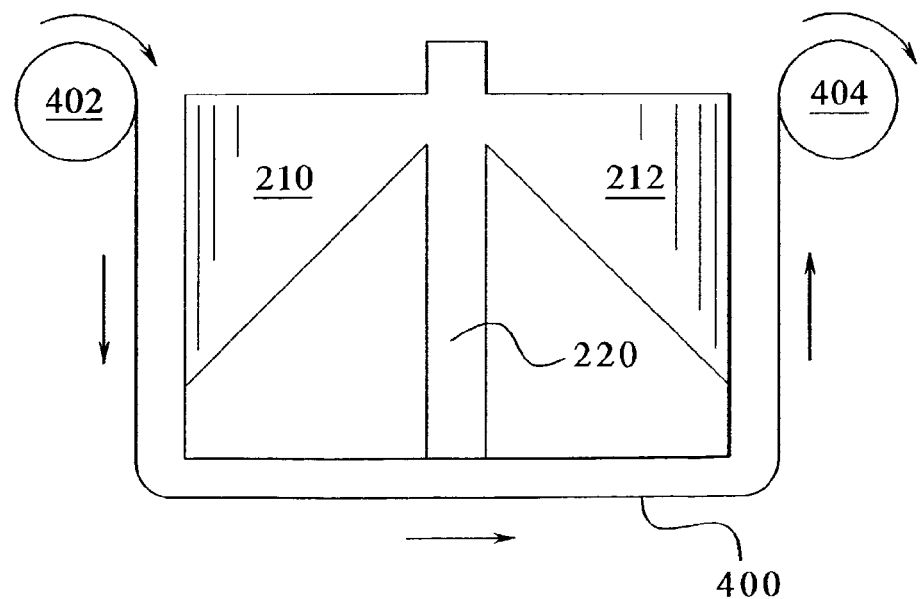
FIG. 6 is a schematic plan view of a protective film according to principles of the present invention.

FIG. 6 shows a protective film 400 according to an embodiment of the invention. The protective film 400 covers the piano convex lenses 210, 212, the anvil 112, and the light pipe 220. The protective film 400 is a thin clear material, preferably, a Mylar® or polyethylene material. The film 400 is provided on, for example, a roll 402 that advances after each disconnection application. When the film 400 advances it is stored in another roll 404. After the roll 402 is used both rolls 402 and 404 can be easily discarded. The laser energy does not have any heating effect on the film. The film 400 does not alter the laser beam characteristics. In this way, the film 400 protects the optics assembly 202 and eliminates cleaning of same. It will be appreciated that one could also achieve this purpose by providing a system of advancing disposable lenses. For example, if the optical assembly includes the light pipe 220 as the anvil 112, the optical assembly could be a number of disposable lenses on a cartridge that rotates after each use. Thus, the used optical assembly is discarded and a new optical assembly is used in each application.

Further Embodiments

Figure 7:
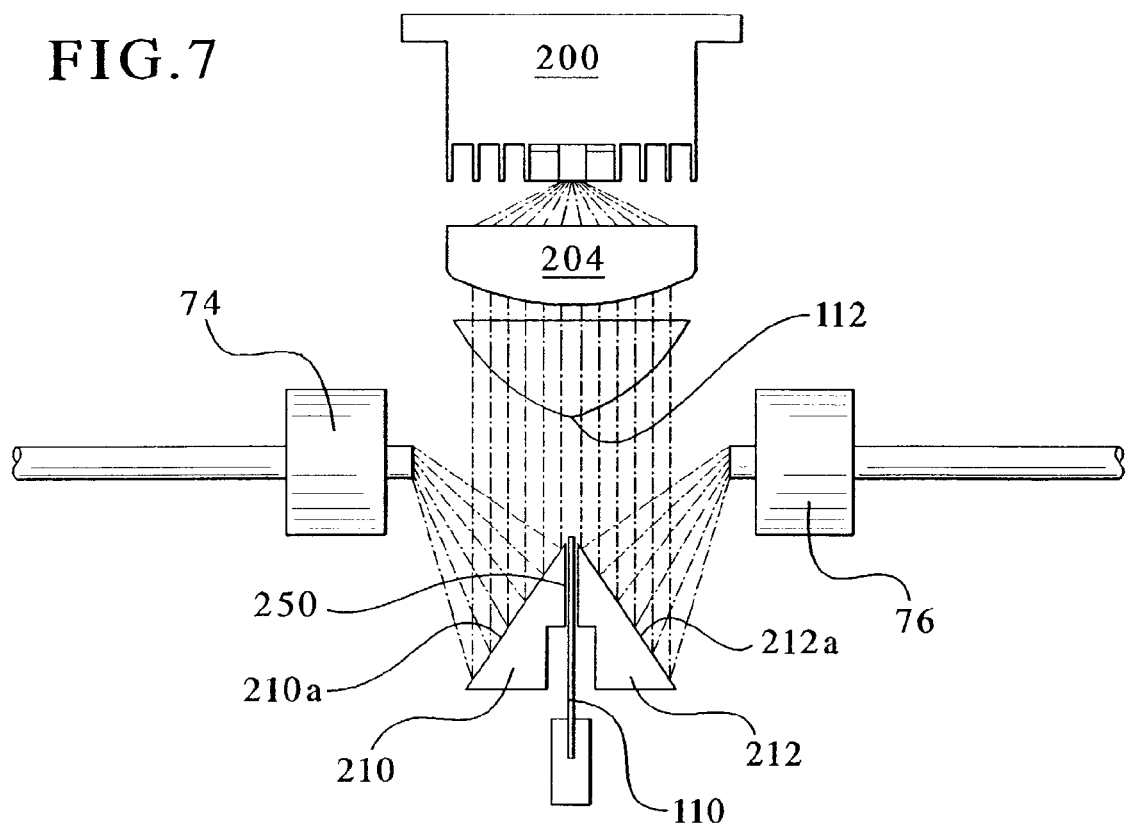
FIG. 7 is a schematic plan view of another embodiment of the present invention.

FIG. 7 illustrates another embodiment of the invention in which the prism 206 and light pipe 220 are not between the tube holders 70, 72 but located near the front 14 of the housing 12. For simplification purposes, FIG. 6 shows the anvil 112 between the collimator 204 and the prism 206. However, during the connection process, the anvil 112 is generally not employed. Instead, the anvil 112 is off to one side 18 or 20 in the housing 12. During the disconnection process, the anvil 112 moves in front of the laser 200. Thus, the anvil 112 may be mounted on a tracking system similar to that described above with respect to the collimator 204.

During the connection process, the prism lens 206 diffuses the laser beam and spreads the energy over a slightly larger area than that described above in FIGS. 4A through 4H. In this example, the lenses 210, 212 are shown with flat reflecting surfaces 210*a*, 212*a*. However, it should be understood that the lenses 210, 212 may be concave or some other configuration depending on the laser type and the need to redirect and focus the beam. Also, the prism 206 may be rough edged lenses 210, 212 to spread the energy at the surface of the sealed tube ends 51. Moreover, another lens (now shown) may be positioned at the surfaces 210*a*, 212*a* between the surface and the tubing to further focus the laser beam. As described above with respect to the embodiment in FIGS. 2A and 2B, the tube ends are brought together after the tube ends are sufficiently heated and a weld is formed. However, the embodiment of FIG. 6 is less complex because it is not necessary to move the prism 206 from in between the tube ends prior to bringing the tube ends together.

During the disconnecting process, the anvil 112 moves in front of the laser 200. The hammer 110 moves through a passageway 250 between the two lenses 210, 212 in the direction of the anvil 112. The hammer 110 compresses the tubing 50 against the anvil 112. In this regard, the remaining steps of the disconnection process are substantially the same as that described above.

Figure 8:
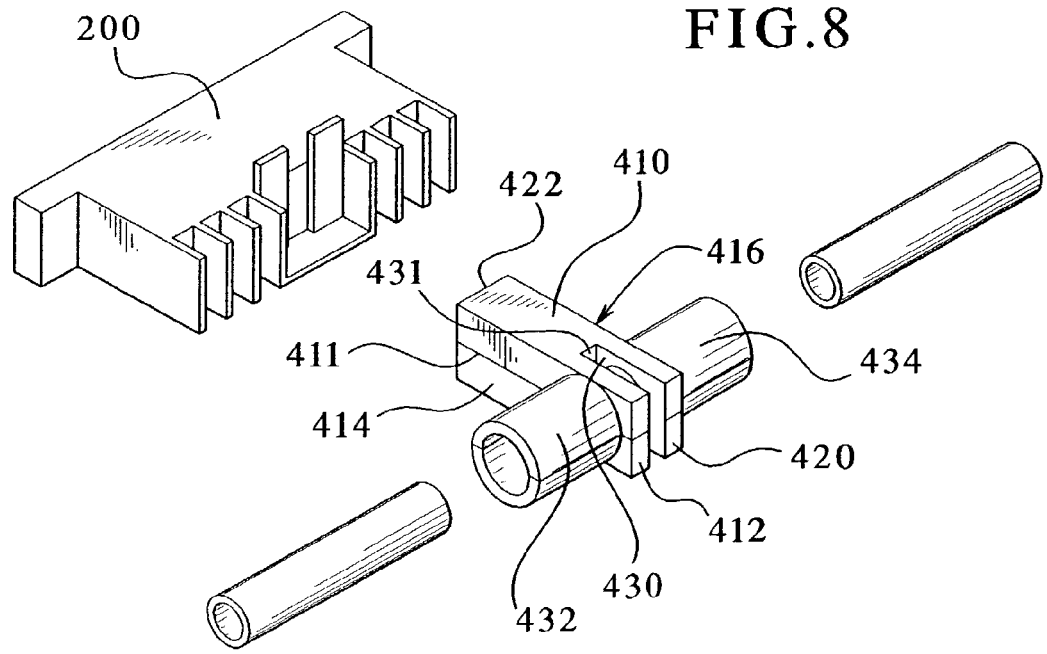
FIG. 8 is a perspective view of an optical assembly of another embodiment of the present invention.

FIG. 8 shows another embodiment of the invention. In this embodiment, the laser optics assembly incorporates a fiber optics assembly 410. The fiber optics assembly can include a large cylinder rod or multiple optical fibers to transmit the electromagnetic energy to the tube and provide the necessary heating and distribution of the energy. In this embodiment, the fiber optics assembly 410 includes a fixed lens 412 with first and second sides 414, 416 and a front and back end 420, 422. A recess or access slot 430 extends from the front end 420 into the assembly 410. The recess 430 ends at wall 431 within the assembly 410. The wall 431 acts as the anvil during the disconnection process. The fiber optics assembly 410 has a parting line 411 in which the assembly may be opened while the tube is loaded for the disconnection process. After the tube 50 is loaded, the recess 430 receives the hammer 110 and the hammer compresses the tube 50 at wall 431. The laser unit 200 is energized and the laser beam is directed down the fixed lens 412 in a similar manner as the light pipe 220 described above. In this way, the crimping and separation process begins.

In addition, a fiber optic member 432, 434 extends perpendicular from each side 414, 416 of the lens 412. During the connection process, the laser unit 200 is energized and the laser beam is directed down the fixed lens 412 to the fiber optic members 432, 434. The fiber optic members 432, 434 emit the laser energy at the tube ends 50. Similar to the embodiment described in FIGS. 2A and 2B above, the assembly 410 moves out from between the tube holders 70, 72 and the tube holders bring the tube ends together to form a weld. If necessary, the laser unit 200 can be energized again and the laser beam is directed down the fixed lens 412 to the area where the tube ends are joined to form a weld.

Figure 9A:
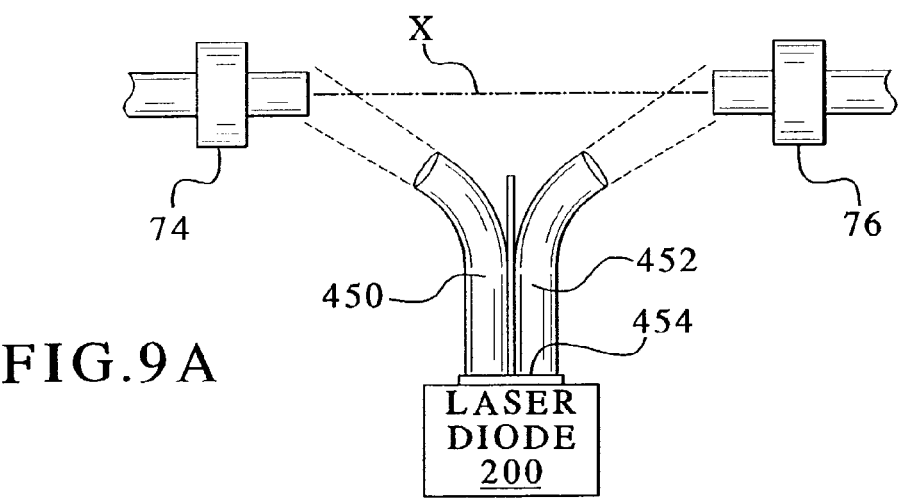
FIGS. 9A and 9B are schematic plan views of another embodiment of the present invention.
Figure 9B:
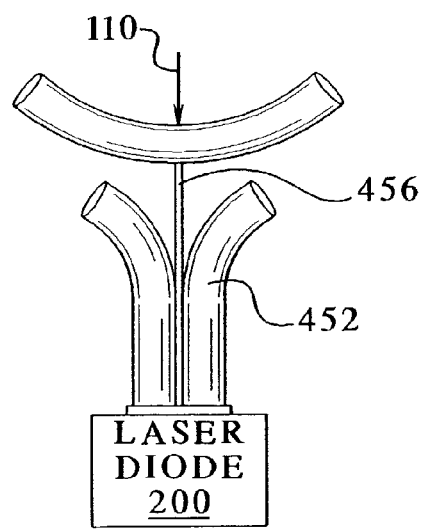

FIGS. 9A and 9B show another embodiment of the invention. In FIG. 9A, an optical assembly 450 is used with the laser unit 200. The optical assembly 450 is adjacent to the laser unit 200 between the laser unit and a plane X that intersects the tubing 50. The optical assembly 450 includes a generally "Y"-shaped optical splitter 452, in which a base 454 of the "Y" is near the output of the laser unit 200. The "Y"-shaped optical splitter extends from the laser unit 200 toward the plane X. The "Y"-shaped optics may be solid fiber optics or individual fibers.

The optical assembly 450 remains stationary during the connection and disconnection operation of the apparatus. During the connection of two tube ends 51, the laser beam is split down the "Y" to each tube end. The tube ends are subsequently brought together for welding. During the disconnection process, the laser beam is directed down a center optical component of the assembly or light pipe 456. Similar to the applications described above, the anvil 110 moves toward the light pipe 456 to compress and pinch the tubing. It is also within the scope of the invention to have the optics assembly 450 as two separate components. In this example, the "Y"-shaped optical splitter 452 and the light pipe 456 are discrete components (not shown). Each component 452, 456 is mounted on a movable plane that moves the required component in front of the laser unit depending on the process to be performed by the apparatus.

Figure 10A:
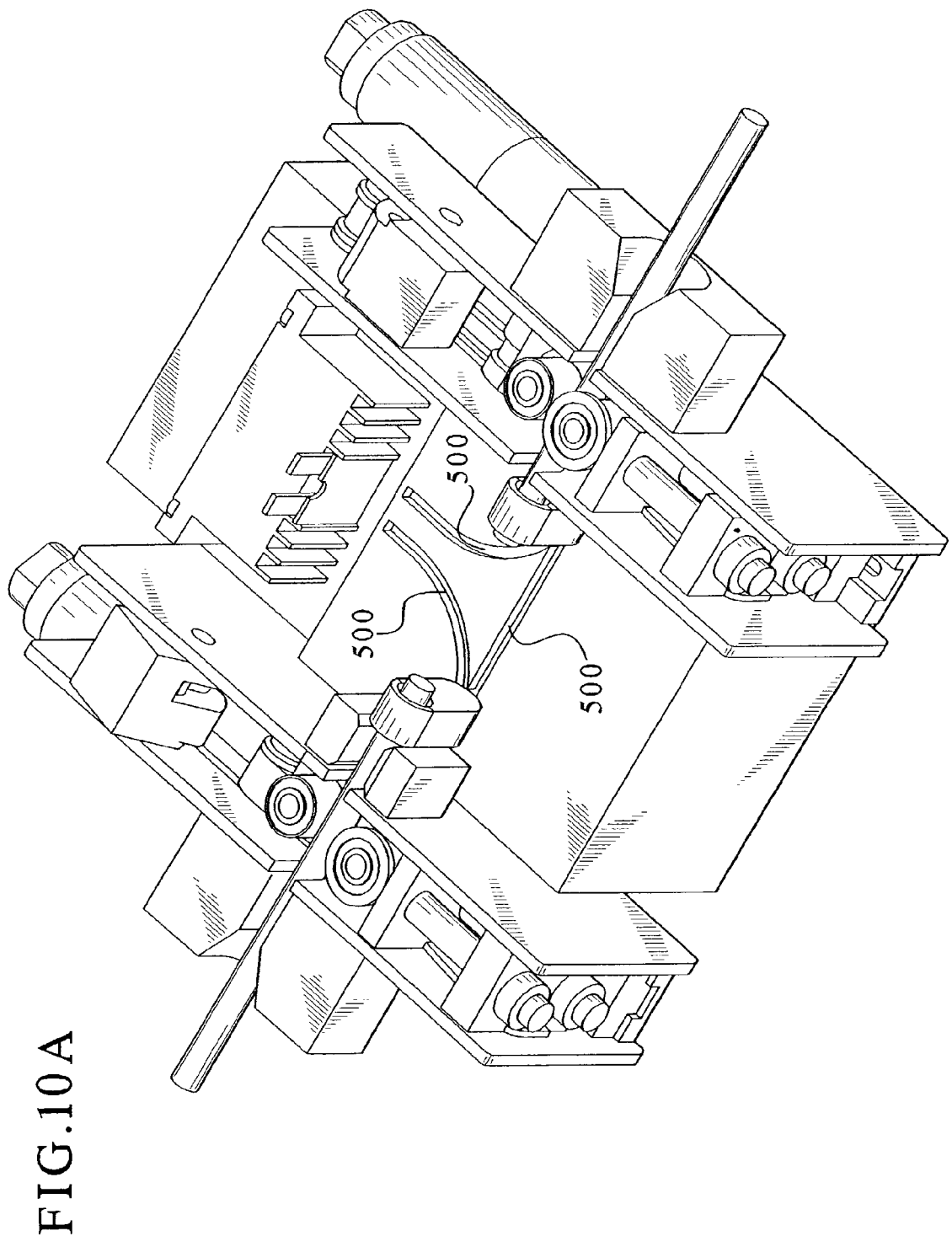
FIGS. 10A and 10B are perspective views of another embodiment of the present invention.
Figure 10B:
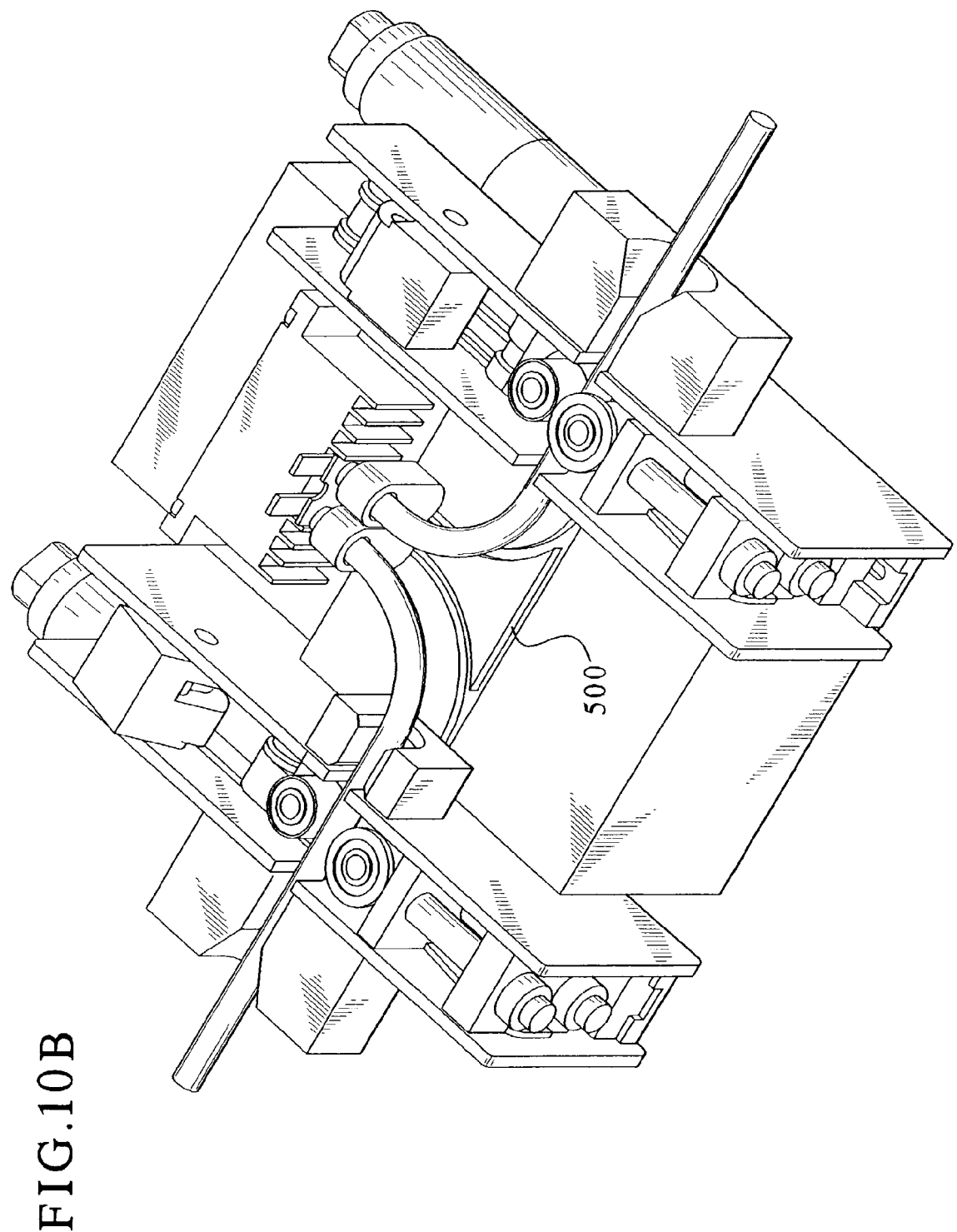

FIGS. 10A and 10B show another embodiment of the invention. In this example, the laser unit 200 is used without the optics assembly. The tube holders 70, 72 are mounted on a track system 500. During the connection process, the track system 500 moves the tube holders 70, 72 along a predetermined path toward the laser unit 200. (FIG. 8B). In this way, the tube holders 70, 72 manipulate the tubes 50 so that the tube ends 51 are, preferably, parallel to each other and face the laser unit 200. Thus, the tube holders 70, 72 rotate approximately 90 degrees from when they receive the tube ends to the point at which the tube ends 51 face the laser unit 200. However, the tube holders may rotate in the range of 70 to 110 degrees and achieve the same results.

The laser unit 200 turns on and melts and sterilizes the tube ends. As discussed above, the tube ends 51 enter the device 10 as sealed tube ends. As such, the tube ends 51 begin to reopen as the laser energy melts this area. The laser unit 200 shuts off once the sensors determine that sufficient heating of the tube ends occurred. At this time, the tube holders 70, 72 retract to their starting position (near guides 56, 58) and then move forward toward each other. The two tube ends 51 come into contact with each other and a weld seal is formed.

Non-PVC, Laser-Weldable Tubing

Figure 11C:
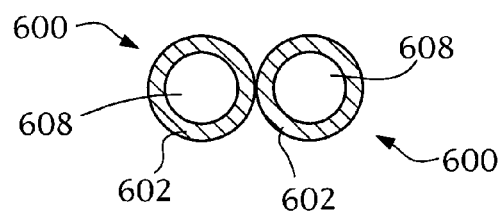

FIGS. 11*a* and 11*b* show a monolayer tubing 600 and a multiple layer tubing 600 respectively that are suitable for use with the present invention. FIG. 11*c* shows a multiple lumen tubing which can have two or more fluid passageways. Like the single lumen tubing of FIGS. 11*a* and 11*b*, the multiple lumen tubing of FIG. 11*c* can be a monolayer structure or a multiple layer structure, and, therefore, it should be understood the following description shall apply to single lumen tubings or multiple lumen tubings.

The monolayer tubing 600 has a sidewall 602 made from a polymeric material and more preferably from a non-PVC containing polymer and most preferably from a non-PVC containing polymer that is capable of heating upon exposure to a laser beam ("laser responsive"). The multiple layer tubing 600 has a first layer or solution contact layer 604 and a second layer 606. At least one of the layers 604 or 606 is composed of a non-PVC containing polymer that is laser responsive. In a preferred form of the invention the other layer 604 or 606 will also be a non-PVC containing polymer, and more preferably a non-PVC containing polymer that heats upon exposure to a laser beam. However, it may also be desirable to have a solution contact layer 604 that is not laser responsive or does not contain any components that may leach into solution or react with the solution. Of course, it is contemplated that tubing having more than two-layers can be used without departing from the scope of the present invention. The tubing sidewalls define a fluid pathway 608 therethrough.

Suitable non-PVC containing polymers include polyolefins, ethylene and lower alkyl acrylate copolymers, ethylene and lower alkyl substituted alkyl acrylate copolymers, ethylene vinyl acetate copolymers, polybutadienes, polyesters, polyamides, and styrene and hydrocarbon copolymers.

Suitable polyolefins include homopolymers and copolymers obtained by polymerizing alpha-olefins containing from 2 to 20 carbon atoms, and more preferably from 2 to 10 carbons. Therefore, suitable polyolefins include polymers and copolymers of propylene, ethylene, butene-1, pentene-1, 4-methyl-1-pentene, hexene-1, heptene-1, octene-1, nonene-1 and decene-1. Most preferably the polyolefin is a homopolymer or copolymer of propylene or a homopolymer or copolymer of polyethylene.

Suitable homopolymers of polypropylene can have a stereochemistry of amorphous, isotactic, syndiotactic, atactic, hemiisotactic or stereoblock. In a more preferred form of the invention, the polypropylene will have a low heat of fusion from about 20 joules/gram to about 220 joules/gram, more preferably from about 60 joules/gram to about 160 joules/gram and most preferably from about 80 joules/gram to about 130 joules/gram. It is also desirable, in a preferred form of the invention, for the polypropylene homopolymer to have a melting point temperature of less than about 165° C. and more preferably from about 130° C. to about 160° C., more preferably from about 140° C. to about 150° C. In one preferred form of the invention, the homopolymer of polypropylene is obtained using a single site catalyst.

Suitable copolymers of propylene are obtained by polymerizing a propylene monomer with an α-olefin having from 2 to 20 carbons. In a more preferred form of the invention, the propylene is copolymerized with ethylene in an amount by weight from about 1% to about 20%, more preferably from about 1% to about 10% and most preferably from 2% to about 5% by weight of the copolymer. The propylene and ethylene copolymers may be random or block copolymers. The propylene copolymer should have a low heat of fusion of from about 40 joules/gram to about 140 joules/gram, more preferable from about 60 joules/gram to about 90 joules/gram. In a preferred form of the invention, the propylene copolymer is obtained using a single-site catalyst.

It is also possible to use a blend of polypropylene and α-olefin copolymers wherein the propylene copolymers can vary by the number of carbons in the α-olefin. For example, the present invention contemplates blends of propylene and α-olefin copolymers wherein one copolymer has a 2 carbon α-olefin and another copolymer has a 4 carbon α-olefin. It is also possible to use any combination of α-olefins from 2 to 20 carbons and more preferably from 2 to 8 carbons. Accordingly, the present invention contemplates blends of propylene and α-olefin copolymers wherein a first and second α-olefins have the following combination of carbon numbers: 2 and 6, 2 and 8, 4 and 6, 4 and 8. It is also contemplated using more than 2 polypropylene and a olefin copolymers in the blend. Suitable polymers can be obtained using a catalloy procedure.

It may also be desirable to use a high melt strength polypropylene. High melt strength polypropylenes can be a homopolymer or copolymer of polypropylene having a melt flow index within the range of 10 grams/10 min. to 800 grams/10 min., more preferably 30 grams/10 min. to 200 grams/10 min, or any range or combination of ranges therein. High melt strength polypropylenes are known to have free-end long chain branches of propylene units. Methods of preparing polypropylenes which exhibit a high melt strength characteristic have been described in U.S. Pat. Nos. 4,916,198; 5,047,485; and 5,605,936 which are incorporated herein by reference and made a part hereof. One such method includes irradiating a linear propylene polymer in an environment in which the active oxygen concentration is about 15% by volume with high energy ionization energy radiation at a dose of 1 to $10^4$ megarads per minute for a period of time sufficient for a substantial amount of chain scission of the linear propylene polymer to occur but insufficient to cause the material to become gelatinous. The irradiation results in chain scission. The subsequent recombination of chain fragments results in the formation of new chains, as well as joining chain fragments to chains to form branches. This further results in the desired free-end long chain branched, high molecular weight, non-linear, propylene polymer material. Radiation is maintained until a significant amount of long chain branches form. The material is then treated to deactivate substantially all the free radicals present in the irradiated material.

High melt strength polypropylenes can also be obtained as described in U.S. Pat. No. 5,416,169, which is incorporated in its entirety herein by reference and made a part hereof, when a specified organic peroxide (di-2-ethylhexyl peroxydicarbonate) is reacted with a polypropylene under specified conditions, followed by melt-kneading. Such polypropylenes are linear, crystalline polypropylenes having a branching coefficient of substantially 1, and, therefore, has no free end long-chain branching and will have a intrinsic viscosity of from about 2.5 dl/g to 10 dl/g.

Suitable homopolymers of ethylene include those having a density of greater than 0.915 g/cc and includes low density polyethylene (LDPE), medium density polyethylene (MDPE) and high density polyethylene (HDPE).

Suitable copolymers of ethylene are obtained by polymerizing ethylene monomers with an α-olefin having from 3 to 20 carbons, more preferably 3–10 carbons and most preferably from 4 to 8 carbons. It is also desirable for the copolymers of ethylene to have a density as measured by ASTM D-792 of less than about 0.915 g/cc and more preferably less than about 0.910 g/cc and even more preferably less than about 0.900 g/cc. Such polymers are oftentimes referred to as VLDPE (very low density polyethylene) or ULDPE (ultra low density polyethylene). Preferably the ethylene α-olefin copolymers are produced using a single site catalyst and even more preferably a metallocene catalyst systems. Single site catalysts are believed to have a single, sterically and electronically equivalent catalyst position as opposed to the Ziegler-Natta type catalysts which are known to have a mixture of catalysts sites. Such single-site catalyzed ethylene α-olefins are sold by Dow under the trade name AFFINITY, DuPont Dow under the trademark ENGAGE® and by Exxon under the trade name EXACT. These copolymers shall sometimes be referred to herein as m-ULDPE.

Suitable copolymers of ethylene also include ethylene and lower alkyl acrylate copolymers, ethylene and lower alkyl substituted alkyl acrylate copolymers and ethylene vinyl acetate copolymers having a vinyl acetate content of from about 8% to about 40% by weight of the copolymer. The term "lower alkyl acrylates" refers to comonomers having the formula set forth in Diagram 1:

Diagram 1

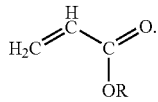

The R group refers to alkyls having from 1 to 17 carbons. Thus, the term "lower alkyl acrylates" includes but is not limited to methyl acrylate, ethyl acrylate, butyl acrylate and the like.

The term "alkyl substituted alkyl acrylates" refers to comonomers having the formula set forth in Diagram 2:

Diagram 2

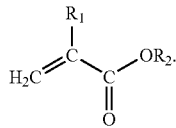

$R_1$ and $R_2$ are alkyls having 1–17 carbons and can have the same number of carbons or have a different number of carbons. Thus, the term "alkyl substituted alkyl acrylates" includes but is not limited to methyl methacrylate, ethyl methacrylate, methyl ethacrylate, ethyl ethacrylate, butyl methacrylate, butyl ethacrylate and the like.

Suitable polybutadienes include the 1,2- and 1,4-addition products of 1,3-butadiene (these shall collectively be referred to as polybutadienes). In a more preferred form of the invention, the polymer is a 1,2-addition product of 1,3 butadiene (these shall be referred to as 1,2 polybutadienes). In an even more preferred form of the invention, the polymer of interest is a syndiotactic 1,2-polybutadiene and even more preferably a low crystallinity, syndiotactic 1,2 polybutadiene. In a preferred form of the invention, the low crystallinity, syndiotactic 1,2 polybutadiene will have a crystallinity less than 50%, more preferably less than about 45%, even more preferably less than about 40%, even more preferably the crystallinity will be from about 13% to about 40%, and most preferably from about 15% to about 30%. In a preferred form of the invention, the low crystallinity, syndiotactic 1,2 polybutadiene will have a melting point temperature measured in accordance with ASTM D 3418 from about 70° C. to about 120° C. Suitable resins include those sold by JSR (Japan Synthetic Rubber) under the grade designations: JSR RB 810, JSR RB 820, and JSR RB 830.

Suitable polyesters include polycondensation products of di-or polycarboxylic acids and di or poly hydroxy alcohols or alkylene oxides. In a preferred form of the invention, the polyester is a polyester ether. Suitable polyester ethers are obtained from reacting 1,4 cyclohexane dimethanol, 1,4 cyclohexane dicarboxylic acid and polytetramethylene glycol ether and shall be referred to generally as PCCE. Suitable PCCE's are sold by Eastman under the trade name ECDEL. Suitable polyesters further include polyester elastomers which are block copolymers of a hard crystalline segment of polybutylene terephthalate and a second segment of a soft (amorphous) polyether glycols. Such polyester elastomers are sold by Du Pont Chemical Company under the trade name HYTREL®.

Suitable polyamides include those that result from a ring-opening reaction of lactams having from 4–12 carbons. This group of polyamides therefore includes nylon 6, nylon 10 and nylon 12. Acceptable polyamides also include aliphatic polyamides resulting from the condensation reaction of di-amines having a carbon number within a range of 2–13, aliphatic polyamides resulting from a condensation reaction of di-acids having a carbon number within a range of 2–13, polyamides resulting from the condensation reaction of dimer fatty acids, and amide containing copolymers. Thus, suitable aliphatic polyamides include, for example, nylon 66, nylon 6,10 and dimer fatty acid polyamides.

The styrene of the styrene and hydrocarbon copolymer includes styrene and the various substituted styrenes including alkyl substituted styrene and halogen substituted styrene. The alkyl group can contain from 1 to about 6 carbon atoms. Specific examples of substituted styrenes include alpha-methylstyrene, beta-methylstyrene, vinyltoluene, 3-methylstyrene, 4-methylstyrene, 4-isopropylstyrene, 2,4-dimethylstyrene, o-chlorostyrene, p-chlorostyrene, o-bromostyrene, 2-chloro-4-methylstyrene, etc. Styrene is the most preferred.

The hydrocarbon portion of the styrene and hydrocarbon copolymer includes conjugated dienes. Conjugated dienes which may be utilized are those containing from 4 to about 10 carbon atoms and more generally, from 4 to 6 carbon atoms. Examples include 1,3-butadiene, 2-methyl-1,3-butadiene (isoprene), 2,3-dimethyl-1,3-butadiene, chloroprene, 1,3-pentadiene, 1,3-hexadiene, etc. Mixtures of these conjugated dienes also may be used such as mixtures of butadiene and isoprene. The preferred conjugated dienes are isoprene and 1,3-butadiene.

The styrene and hydrocarbon copolymers can be block copolymers including di-block, tri-block, multi-block, and star block. Specific examples of diblock copolymers include styrene-butadiene, styrene-isoprene, and the hydrogenated derivatives thereof. Examples of triblock polymers include styrene-butadiene-styrene, styrene-isoprene-styrene, alpha-methylstyrene-butadiene-alpha-methylstyrene, and alpha-methylstyrene-isoprene-alpha-methylstyrene and hydrogenated derivatives thereof.

The selective hydrogenation of the above block copolymers may be carried out by a variety of well known processes including hydrogenation in the presence of such catalysts as Raney nickel, noble metals such as platinum, palladium, etc., and soluble transition metal catalysts. Suitable hydrogenation processes which can be used are those wherein the diene-containing polymer or copolymer is dissolved in an inert hydrocarbon diluent such as cyclohexane and hydrogenated by reaction with hydrogen in the presence of a soluble hydrogenation catalyst. Such procedures are described in U.S. Pat. Nos. 3,113,986 and 4,226,952, the disclosures of which are incorporated herein by reference and made a part hereof.

Particularly useful hydrogenated block copolymers are the hydrogenated block copolymers of styrene-isoprene-styrene, such as a styrene-(ethylene/propylene)-styrene block polymer. When a polystyrene-polybutadiene-polystyrene block copolymer is hydrogenated, the resulting product resembles a regular copolymer block of ethylene and 1-butene (EB). As noted above, when the conjugated diene employed is isoprene, the resulting hydrogenated product resembles a regular copolymer block of ethylene and propylene (EP). One example of a commercially available selectively hydrogenated is KRATON G-1652 which is a hydrogenated SBS triblock comprising 30% styrene end blocks and a midblock equivalent is a copolymer of ethylene and 1-butene (EB). This hydrogenated block copolymer is often referred to as SEBS. Other suitable SEBS or SIS copolymers are sold by Kurrarry under the tradename SEPTON® and HYBRAR®.

It may also be desirable to use graft modified styrene and hydrocarbon block copolymers by grafting an alpha,beta-unsaturated monocarboxylic or dicarboxylic acid reagent onto the selectively hydrogenated block copolymers described above.

The block copolymers of the conjugated diene and the vinyl aromatic compound are grafted with an alpha,beta-unsaturated monocarboxylic or dicarboxylic acid reagent. The carboxylic acid reagents include carboxylic acids per se and their functional derivatives such as anhydrides, imides, metal salts, esters, etc., which are capable of being grafted onto the selectively hydrogenated block copolymer. The grafted polymer will usually contain from about 0.1 to about 20%, and preferably from about 0.1 to about 10% by weight based on the total weight of the block copolymer and the carboxylic acid reagent of the grafted carboxylic acid. Specific examples of useful monobasic carboxylic acids include acrylic acid, methacrylic acid, cinnamic acid, crotonic acid, acrylic anhydride, sodium acrylate, calcium acrylate and magnesium acrylate, etc. Examples of dicarboxylic acids and useful derivatives thereof include maleic acid, maleic anhydride, fumaric acid, mesaconic acid, itaconic acid, citraconic acid, itaconic anhydride, citraconic anhydride, monomethyl maleate, monosodium maleate, etc.

The styrene and hydrocarbon block copolymer can be modified with an oil such as the oil modified SEBS sold by the Shell Chemical Company under the product designation KRATON G2705.

In one preferred form of the invention, the tubing is composed of a multiple component polymer blend. The present invention contemplates blending two or more of any of the polymers set forth above. In a preferred form of the invention, the polymer blend includes a polyolefin blended with a styrene and hydrocarbon copolymer. In a preferred form of the invention, the polyolefin is a propylene containing polymer and can be selected from the homopolymers and copolymers of propylene described above including high melt strength polypropylenes. It may also be desirable to have three or more components including a styrene and hydrocarbon copolymer with a blend of various types of polypropylenes. The polypropylene, either alone or in sum, can be present in an amount by weight of the blend from about 10% to about 50%, more preferably from about 15% to about 45% and most preferably from about 20% to about 40% with the balance of the blend being the styrene and hydrocarbon block copolymer.

When using oil modified SEBS it may be desirable, though not critical, to use a high melt strength polypropylene as a blend component. Suitable polypropylene and SEBS containing blends include: (1) precompounded blends of PP and SEBS sold by Wittenburg under the trade name CAWITON and particularly grades PR 3670E and PR4977; (2) from 90–98% by weight KRATON G2705 with 2–10% Basell PROFAX PF 611 high melt strength polypropylene; (3) 75% KRATON G2705 with 23% Basell PROFAX SA 861 random copolymer of propylene and ethylene with 2% Basell PROFAX PF-611 which is high melt strength PP; and (4) precompounded blend of PP/SEBS sold by J-Von under grade 70585 E.

In another preferred form of the invention the tubing will be fabricated from a single m-ULDPE resin or a blend of m-ULDPE resins. One particularly suitable m-ULDPE resin is sold by DuPont-Dow under the trademark ENGAGE® and even more particularly ENGAGE® 8003 (density 0.885 g/cc). It is also contemplated blending more than one m-ULDPE resins. Such resins and tubings and film made therefrom are more fully set forth in U.S. Pat. No. 6,372,848 which is incorporated in its entirety herein by reference and made a part hereof.

It is also contemplated fabricating tubing from polybutadienes or blends of polybutadiene resins described above.

Because the suitable non-PVC containing polymers and polymer blends are typically not laser responsive one must incorporate into the polymer or polymer blend a laser responsive component. Suitable laser-responsive components include dyes, colorants and/or pigments. In a more preferred form of the invention, the laser responsive material is a dye and more preferably an organic dye having a functional group that is responsive to a laser beam at a wavelength, or a narrow range of wavelengths, within a range of wavelengths in the near infrared spectrum and more preferably from about 700 nm to about 1500 nm. Representative functional groups include polymethine, porphine, indanthrene, quinone, di- and tri-phenylmethane, and metal complexed dithiol dyes. In a preferred form of the invention, the dye will have an absorptivity of higher than about 50 (optical density/gram) when exposed to a laser beam providing light in the frequency range in which the dye is responsive. In a preferred form of the invention, the dye is responsive to a laser beam at peak wavelengths from about 780 nm to about 810 nm and generates sufficient heat over a short period of time to allow for melting of the non-PVC polymer or polymer blend. What is meant by short period of time is less than 15 seconds.

The dyes are preferably sparingly soluble or insoluble in an aqueous medium including water, saline solutions, dextrose solutions, lipid containing solutions and protein containing solutions so if they form a part of the solution contact layer they will not readily leach into the solution in a significant or deleterious amount. The dyes are also preferably thermally stable at temperatures reached during extrusion processing of the polymer or polymer blend. Suitable dyes are sold by Epolin Inc. under the trade name EPOLIGHT 4121 and 4149. When using a laser responsive material with an absorption of higher than about 50, only low quantities of such dye material is required and typically is added to the tubing blend in an amount from about 20 ppm to about 500 ppm, more preferably from about 100 ppm to about 400 ppm and most preferably from about 200 ppm to about 300 ppm. It is contemplated using a laser responsive material having an absorptivity of less than 50 but one would have to use higher concentrations of the laser responsive material. It is also contemplated using other dyes that are not responsive to the laser but are used for color coding purposes described above.

In another preferred form of the invention, the laser responsive material will be applied to a surface of materials to be joined instead of incorporating the laser responsive material into the blend. To this end, the laser responsive material is dissolved or suspended in a suitable carrier or solvent, and, in this form can be applied specifically to selected portions of the surfaces to be joined. The laser responsive material can be applied by dipping the surfaces to be joined into the laser responsive material, or the laser responsive material can be brushed on, sprayed on, printed on or the like.

The tubings of the present invention can be manufactured by any known polymer processing technique, but, in a preferred form of the invention, is formed by extrusion, coextrusion or injection molding. Such tubings are soft, flexible, kink resistant, have a good touch feeling (haptics), and are capable of being sterilized by steam sterilization, radiation or by ethylene oxide (EtO) exposure.

Non-PVC, Laser Weldable End Cap Film

FIG. 12 shows the tubing 600 with an end cap 610 hermetically sealed thereto. The end cap film 610 is a monolayer or multiple layer polymeric film that has a tubing contacting surface 611 that is adhesively compatible with the tubing 600. The end cap film can be formed by any suitable polymer processing technique including extrusion, coextrusion, extrusion lamination, lamination, injection molding and the like. The end cap film 610, in a preferred form of the invention, is attached with sufficient strength to an end surface of tubing to withstand a burst strength of 30 psi. Burst strength is measured by applying pressurized air through a tubing flowpath 613 to pressurize the tubing until the tubing or end cap ruptures or leaks. The end cap 610 can be dimensioned to exceed the dimension of the end of the tubing and excess material is wrapped around the tubing end where it is attached to the tubing sidewalls 602 to form the drum embodiment referred to above. It is also possible to dimension the cap 610 as shown in FIG. 12 to match the dimension of the end of the tubing and be attached only to the end portion of the tubing without any significant amount of excess material.

The end cap 610 can be fabricated from single polymers such as the m-ULDPE resins described above. Such and end cap made from m-ULDPE are particularly well suited for use with m-ULDPE tubing containing blends. The end cap 610 can also be fabricated from polymer blends having at least a first component and a second component. The first component is selected from: (1) ethylene and α-olefin copolymers having a density of less than about 0.915 g/cc, (2) ethylene and lower alkyl acrylate copolymers, (3) ethylene and lower alkyl substituted alkyl acrylate copolymers and (4) ionic polymers, commonly referred to as ionomers. The term "ionomer" is used herein to refer to metal salts of the acrylic acid copolymers having pendent carboxylate groups associated with monovalent or divalent cations such as zinc or sodium. The first component is present in an amount from about 99% to about 50% by weight of the blend, more preferably from about 85%–50% and most preferably from about 70%–50%.

The second component is selected from the group consisting of: (1) propylene containing polymers, (2) butene containing polymers, (3) polymethyl pentene containing polymers, (4) cyclic olefin containing polymers and (5) bridged polycyclic hydrocarbon containing polymers. The second component is present in an amount by weight of the blend from about 50% to about 1%, more preferably from about 50%–15% and most preferably from about 30%–50%. These polymer blends for the end cap are particularly well suited for use with the tubings made from blends of polyolefin and styrene and hydrocarbon copolymers.

Suitable homopolymer and copolymers of cyclic olefins and bridged polycyclic hydrocarbons and blends thereof can be found in U.S. Pat. Nos. 4,874,808; 5,003,019; 5,008,356; 5,288,560; 5,218,049; 5,854,349; 5,863,986; 5,795,945; and 5,792,824, which are incorporated in their entirety herein by reference and made a part hereof.

In a preferred form of the invention, suitable cyclic olefin monomers are monocyclic compounds having from 5 to about 10 carbons in the ring. The cyclic olefins can be selected from the group consisting of substituted and unsubstituted cyclopentene, cyclopentadiene, cyclohexene, cyclohexadiene, cycloheptene, cycloheptadiene, cyclooctene, and cyclooctadiene.

In a preferred form of the invention, suitable bridged polycyclic hydrocarbon monomers have two or more rings and more preferably contain at least 7 carbons. The rings can be substituted or unsubstituted. Suitable substitutes include lower alkyl, aryl, aralkyl, vinyl, allyloxy, (meth) acryloxy and the like. The bridged polycyclic hydrocarbons are selected from the group consisting of those disclosed in the above incorporated patents. Suitable bridged polycyclic hydrocarbon containing polymers are sold by Ticona under the tradename TOPAS, by Nippon Zeon under the tradename ZEONEX and ZEONOR, by Daikyo Gomu Seiko under the tradename CZ resin, and by Mitsui Petrochemical Company under the tradename APEL.

In a preferred form of the invention, the end cap will be a monolayer film from a blend by weight of from about 35% to about 45% of a ethylene and α-olefin copolymer having a density of less than about 0.900 g/cc, from about 20% to about 30% of an ethylene and α-olefin copolymer having a density of higher than about 0.900 g/cc but less than about 0.910 g/cc, and from about 30% to about 40% polypropylene, and more preferably a random copolymer of propylene with approximately 3% by weight of an ethylene comomoner. The end cap should have a thickness from about 3 mils to about 10 mils.

Because these end cap materials are not laser responsive, one of the laser responsive dyes must be incorporated into the single polymer or polymer blends for the end cap. For the end cap material, the dye should be incorporated in an amount from about 200 ppm to about 2000 ppm, more preferably from about 400 ppm to about 1800 ppm and most preferably from about 500 ppm to about 1000 ppm.

Coupler

FIG. 13 shows a coupler 620 having opposed tubing mounting portions 622, a tubing stop 624 and a fluid pathway 626 therethrough. As shown in FIG. 14, the coupler can be used to connect a first tubing to a second tubing even when the first and second tubings are incompatible with one another. The assembly shown in FIG. 14 will be discussed in greater detail below. The tubing mounting portions 622 can have a tapered portion at its distal end for ease of mounting a tubing thereto. The surface of the coupler 620 can be textured or have a matte finish for ease of mounting of the tubing. The tubing mounting portions 622 are shown to have relatively the same length but could have different lengths without departing from the scope of the present invention. It is also contemplated the tubing mounting portions 622 can have ridges or other protuberances for heat concentrating or enhancing an interference fit between the tubing and the tubing mounting portions 622.

The tubing mounting portions 622 are shown to be concentrically mounted with respect to one another and with respect to the fluid pathway 626. It is contemplated the coupler can have numerous shapes where the tubing portions 622 are not concentrically disposed with respect to one another. It is contemplated one tubing mounting portion can have a first axis and the other tubing mounting portion will have a second axis transverse to the first axis. What is meant by transverse is one axis extends in a direction to intersect the second axis even if the axis will not intersect it. It is also contemplated the coupler can have more than two tubing mounting portions, more than one tubing stop and more than one fluid pathway. It is desirable the tubing when attached to the coupler have a bond strength in excess of 15 lbf when tested by a pull test. An assembly fails the pull test if the tubing breaks or become detached from the coupler at a pull force below 15 lbf.

The coupler is composed of a non-PVC polymeric material selected from the materials set forth above for the tubing and preferably is composed of a polymer blend. In one preferred form of the invention the tubing has two components of from about 40% to about 60% EVA and a second component of from about 60% to about 40% of a polyester, polyester elastomer, or a polyurethane. The EVA, preferably, has a modifier group associated therewith and selected from the group consisting of: aromatic hydrocarbons, carbon dioxide, monoethylenically unsaturated hydrocarbons, acrylonitriles, vinyl ethers, vinyl esters, vinylamides, vinyl ketones, vinyl halides, epoxides, carboxylic acids and anhydride derivatives thereof (including fused ring carboxylic acid anhydrides). Most preferably, the modifier group is maleic acid or maleic anhydride.

In another preferred form of the invention the polymer blend has three components. The first component is a polyolefin and more preferably a propylene containing polymer in an amount by weight of from about 25% to about 35% such as those sold by Solvay under the trade name FORTILENE and most particularly FORTILENE grade KS 490. The second component is a polyester and more preferably a polyester elastomer such as those sold by DuPont under the tradename HYTREL® and in an amount by weight of the blend of from about 35% to about 45%. The second component can also be a polyurethane. The third component is an ethylene vinyl acetate copolymer having a vinyl acetate content of from about 8% VA to about 40% vinyl acetate, and more preferably a carboxylic acid modified EVA or a carboxylic acid anhydride modified EVA. The EVA is present in an amount by weight of the blend of from about 25% to about 35%. The present invention further contemplates acid modifying or carboxylic acid anhydride modifying the propylene first component instead of or in addition to such modification to the EVA. The coupler 620 can be made by polymer processing techniques such as injection molding.

Suitable polyurethanes include both aromatic and aliphatic type polyurethanes. Suitable polyurethanes are formed by reacting diisocyanate with a chain extender. Diisocyanates include: Diphenylmethane diisocyanate (MDI), toluene diisocyanate (TDI), hexylene diisocyanate (HDI), and isophorone diisocyanate (IPDI). Chain Extenders include diol type, diamine type, polyester containing polyols and polyether containing polyols. The diol type include: 1,4-butane diol, ethylene glycol, 1,6-hexane diol and 1,4-bis-beta-hydroxyethoxybenzene. The diamine type include aliphatic and aromatic type. Aliphatic type includes ethylene diamine. Aromatic type includes: toluylene diamine and diaminodiphenylmethane.

Laser-Weldable Tubing Assemblies and Therapeutic Fluid Delivery Sets

FIG. 14 shows a tubing assembly 628 having a first laser weldable tubing 600 and a second tubing 630 which are connected together and placed in fluid communication by the coupler 620. The second tubing 630 is made from a material incompatible with the material of tubing 600. What is meant by incompatible is the materials are not capable of being directly joined together in a secure fashion utilizing conductive or inductive heat sealing techniques. This assembly 628 is particularly well suited for joining a PVC tubing 630 from a fluid delivery set or peritoneal dialysis set with the laser weldable, non-PVC tubing 600 described above. The laser weldable tubing 600 can be connected to a transfer set of a patient using the laser welding device 10 discussed above.

The first and second tubing 600, 630 can be connected to the coupler by sliding the fluid pathway 608 of the tubings over the tubing mounting portions 622 until an end portion of the tubing contacts the tubing stop 624. The tubings 600 and 630 are then fixedly attached to the coupler by heat sealing such as with a ring-shaped die, radio frequency heat sealing, solvent bonding, adhesive bonding, or by heating the tubing and coupler in an autoclave during a steam sterilization process (i.e., 121° C. for 1 hour) or other suitable techniques. When heat sealing a mandrel may be employed to maintain the shape of the coupler and tubing assembly.

FIG. 15 shows a fluid container 640 such as a therapeutic fluid container for storing a dialysate solution, a drain bag of a peritoneal dialysis set, an I.V. container, a blood container, a blood component container a blood substitute container or the like, in fluid communication with a laser weldable tubing 600.

FIG. 16 shows the laser-weldable tubing 600 connected to a tubing 650 from a peritoneal dialysis transfer set. The tubing connection is made with the device 10 as described in detail above.

Figure 17:
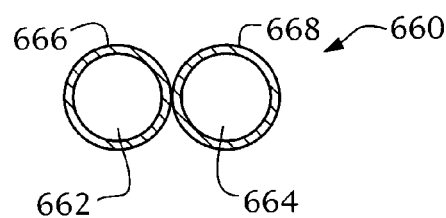
FIG. 17 is a cross-sectional view of a dual lumen tubing.

FIG. 17 shows a laser-weldable dual lumen tubing 660 having first and second fluid passageways 662 and 664 and first and second lumen 666 and 668 attached together. It is contemplated that more than two lumen, such as three, four or five or more, could be attached together without departing from the scope of the present invention. The first and second lumen are connected along peripheral edges and can extend parallel with respect to one another along a length of the tubing or the first and second lumen can be helically disposed with respect to one another or otherwise braided.

Figure 18:
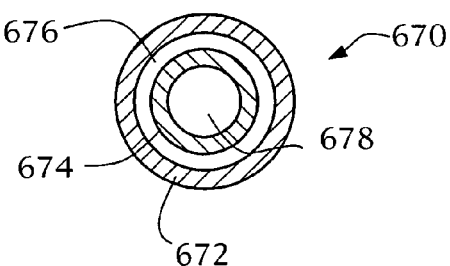
FIG. 18 is a cross-sectional view of a dual lumen tubing with the individual lumen concentrically disposed with respect to one another.

FIG. 18 shows another embodiment of a laser-weldable dual lumen tubing 670 having a first and second lumen 672 and 674 having, respectively, first and second fluid passageways 676 and 678. The first and second lumen 672 and 674 are concentrically disposed with respect to one another. It is contemplated that more than two lumen could be concentrically mounted without departing from the present invention.

Figure 19:
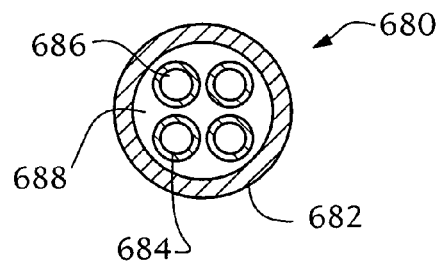
FIG. 19 is a cross-sectional view of a multiple lumen tubing.

FIG. 19 shows yet another embodiment of a laser-weldable, multiple lumen tubing 680 having a primary lumen 682 and four secondary lumen 684 each having a fluid passageway 686. The term "multiple" is meant to include 2 or more so a dual lumen tubing is a multiple lumen tubing. The area 688 between the secondary lumen 684 can be a fluid passageway or can be material such as packing material to hold the secondary lumen in position. While four secondary lumen are shown it is contemplated that two or more secondary lumen could be provided without departing from the present invention. Also, while the secondary lumen 684 are shown spaced apart from one another one or more of these secondary lumen can be attached together. The secondary lumen 684 can extend in a direction parallel to one another or be helically disposed with respect to one another or otherwise braided together.

EXAMPLES

Example 1

A membrane film was extruded from a polymer blend of 40% by weight of a first m-ULDPE resin (density 0.885 g/cc, Dow VP 8770), 25% by weight of a second m-ULDPE resin (density of 0.902 g/cc, Dow PL 1880), 35% polypropylene (Basell SR-549M) and 600 ppm dye (Epolin 4121). The components were blended in a David Standard twin screw extruder and extruded through a die to a thickness of 0.005 inches. The film was exposed to a diode laser (810 nm), 30 amp for a period of 10 seconds where the film melted.

Example 2

A tubing was extruded from a polymer blend of Cawiton PR 3670 with 200 ppm dye (Epolin 4121). The components were blended in a David Standard twin screw extruder and extruded through a die to a wall thickness 0.039 inches, ID of 0.157 inches, OD of 0.235 inches. The tubing was exposed to a diode laser (810 nm), 30 amp for a period of 10 seconds where the tubing melted.

Example 3

A tubing was extruded in the same manner as in Example 2 except the blend contained 250 ppm of the dye. The tubing was exposed to a diode laser (810 nm), 30 amp for a period of 10 seconds where the tubing melted.

Example 4

A coupler was injection molded from a two component polymer blend of 50% HYTREL (5556 WITH 50% BYNEL 1123. The blend components were pellitized with a 1½ inch David Standard twin screw extruder and injected molded with a 25 ton Arburg injection molding machine. A first tubing of PVC was slid over a first tubing mounting portion and attached to the coupler by radio frequency sealing. A second tubing was fabricated as set forth in Example 2. The second tubing was slid over a second tubing mounting portion of the coupler and then autoclaved at 121° C. for one hour. The assembly was allowed to cool and the first tubing and the second tubing were pulled until the tubing broke or until it became detached from the coupler and the force required to do so was measured respectively at 29.3 lbf and 29.4 lbf.

Example 5

A coupler was injection molded as set forth in Example 4 from a three-component polymer blend of 30% polypropylene (Solvay KS 490), 40% polyester elastomer (HYTREL(W 5556) and 30% anhydride modified EVA (BYNEL 3810). As in Example 4, a first tubing of PVC was slid over a first tubing mounting portion and sealed thereto using radio frequency sealing. A second tubing was fabricated as set forth in Example 2 and was slid over a second tubing mounting portion. The assembly was autoclaved at 121° C. for one hour. The assembly was allowed to cool and the first tubing and the second tubing were pulled until the tubing broke or until it became detached from the coupler and the force required to do so was measured respectively at 48.2 lbf and 34.3 lbf.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A medical fluids delivery assembly comprising:
    a container defining a sealed interior, the sealed interior configured to store a therapeutic fluid; and
    a laser-weldable non-PVC tubing having a void-free sidewall comprising a polymer blend of:
        a first component of a material not thermally responsive to a laser beam and selected from the group consisting of polyolefins, ethylene and lower alkyl acrylate copolymers, ethylene and lower alkyl substituted alkyl acrylate copolymers, ethylene vinyl acetate copolymers, polybutadienes, polyesters, polyamides, and styrene and hydrocarbon copolymers, and
        a second component of a laser responsive material having low solubility in aqueous medium and being sufficiently thermally responsive to exposure to a laser beam having a wavelength within a range from about 700 nm to about 1500 nm to melt a portion of the sidewall upon exposure to the laser beam for a short period of time;
    wherein the laser-weldable tubing is configured to sealingly couple to the container upon exposure to the laser beam to provide a fluid connection between the sealed interior and an interior of the laser weldable tubing.

2. The assembly of claim 1, wherein the therapeutic fluid is selected from the group consisting of a peritoneal dialysis solution, a spent peritoneal dialysis solution, a nutritional solution, blood, blood components, blood substitutes and an IV solution.

3. The assembly of claim 1, further comprising an end cap film forming a fluid tight seal on an end portion of the tubing.

4. The assembly of claim 1, wherein the polyolefin is obtained from a monomer of an α-olefin having from 2 to 20 carbons.

5. The assembly of claim 4, wherein the polyolefin is selected from the group of propylene containing polymers and ethylene containing polymers.

6. The assembly of claim 4, wherein the polyolefin is selected from the group consisting of homopolymers of polypropylene and copolymers of polypropylene.

7. The assembly of claim 6, wherein the homopolymer of polypropylene has a stereochemistry selected from the group consisting of isotactic, syndiotactic, atactic, hemiisotactic and stereoblock.

8. The assembly of claim 6, wherein the copolymer of polypropylene is selected from the group consisting of random copolymers and block copolymers.

9. The assembly of claim 8, wherein the copolymer of polypropylene is obtained by polymerizing a propylene monomer with an α-olefin having from 2 to 20 carbons.

10. The assembly of claim 8, wherein the copolymer of polypropylene is selected from the group of random copolymers with ethylene and block copolymers with ethylene.

11. The assembly of claim 8, wherein the polyolefin has a heat of fusion from about 60 joules/g to about 160 joules/g.

12. The assembly of claim 8, wherein the polyolefin has a peak melting point temperature of less than about 165° C.

13. The assembly of claim 1, wherein the first component is a second blend of a first polypropylene and a styrene and hydrocarbon copolymer.

14. The assembly of claim 13, wherein the styrene and hydrocarbon copolymer is selected from the group of random copolymers of styrene and hydrocarbon and block copolymers of styrene and hydrocarbon.

15. The assembly of claim 14, wherein the styrene and hydrocarbon block copolymer is selected from the group consisting of di-block copolymers, tri-block copolymers, multi-block copolymers and star block copolymers.

16. The assembly of claim 15, wherein the styrene and hydrocarbon block copolymer is oil modified.

17. The assembly of claim 13, wherein the second blend includes a second polypropylene, the second polypropylene having high melt strength.

18. The assembly of claim 17, wherein the second blend has from about 10% to about 50% by weight of the sum of the weights of the first polypropylene and the second polypropylene and the styrene and hydrocarbon copolymer constituting the remaining weight portion of the second blend.

19. The assembly of claim 5, wherein the polyolefin is selected from the group consisting of homopolymers of ethylene and copolymers of ethylene.

20. The assembly of claim 19, wherein the copolymers of ethylene are obtained by polymerizing ethylene monomers with an α-olefin having from 3 to 20 carbons.

21. The assembly of claim 19, wherein the copolymers of ethylene are obtained by polymerizing ethylene monomers with an α-olefin having from 4 to 8 carbons.

22. The assembly of claim 19, wherein the copolymers of ethylene have a density of less than about 0.915 g/cc.

23. The assembly of claim 19, wherein the copolymers of ethylene have a density of less than about 0.900 g/cc.

24. The assembly of claim 19, wherein the polyolefin is an ultra-low density polyethylene.

25. The assembly of claim 24, wherein the ultra-low density polyethylene is obtained utilizing a single-site catalyst.

26. The assembly of claim 25, wherein the ultra-low density polyethylene is obtained utilizing a metallocene catalyst.

27. The assembly of claim 1, wherein the first component is a polybutadiene.

28. The assembly of claim 1, wherein the laser responsive material has a functional group selected from the group polymethine, porphine, indanthrene, quinone, di- and triphenylmethane, and metal complexed dithiol dyes.

29. The assembly of claim 28, wherein the laser responsive material is a dye.

30. The assembly of claim 29, wherein the dye is thermally stable at temperatures reached during extrusion processing of the tubing.

31. The assembly of claim 1 wherein the tubing is a monolumen tubing or a multiple lumen tubing.

32. The assembly of claim 1 wherein the wavelength range is from about 780 nm to about 810 nm.

* * * * *